US009695475B2

(12) United States Patent
Liang et al.

(10) Patent No.: US 9,695,475 B2
(45) Date of Patent: Jul. 4, 2017

(54) COMPETITIVE MODULATION OF MICRORNAS

(71) Applicant: Ionis Pharmaceuticals, Inc., Carlsbad, CA (US)

(72) Inventors: Xue-hai Liang, Del Mar, CA (US); Stanley T. Crooke, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 14/651,344

(22) PCT Filed: Dec. 11, 2013

(86) PCT No.: PCT/US2013/074473
§ 371 (c)(1),
(2) Date: Jun. 11, 2015

(87) PCT Pub. No.: WO2014/093537
PCT Pub. Date: Jun. 19, 2014

(65) Prior Publication Data
US 2015/0299789 A1      Oct. 22, 2015

Related U.S. Application Data

(60) Provisional application No. 61/735,688, filed on Dec. 11, 2012.

(51) Int. Cl.
| | | |
|---|---|---|
| *C07H 21/02* | (2006.01) | |
| *C07H 21/04* | (2006.01) | |
| *C12Q 1/68* | (2006.01) | |
| *A61K 31/7088* | (2006.01) | |
| *A61K 31/7115* | (2006.01) | |
| *A61K 31/712* | (2006.01) | |
| *A61K 31/7125* | (2006.01) | |
| *A61K 31/713* | (2006.01) | |
| *C12N 15/11* | (2006.01) | |
| *C12N 15/113* | (2010.01) | |

(52) U.S. Cl.
CPC ........ *C12Q 1/6876* (2013.01); *A61K 31/7088* (2013.01); *A61K 31/712* (2013.01); *A61K 31/713* (2013.01); *A61K 31/7115* (2013.01); *A61K 31/7125* (2013.01); *C12N 15/111* (2013.01); *C12N 15/113* (2013.01); *C12N 2310/14* (2013.01); *C12N 2310/141* (2013.01); *C12N 2320/11* (2013.01); *C12Q 2600/136* (2013.01); *C12Q 2600/178* (2013.01)

(58) Field of Classification Search
CPC ................ C12N 15/113; C12N 2310/11
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Huynh Dinh et al. |
| 5,130,302 A | 7/1992 | Spielvogel et al. |
| 5,134,066 A | 7/1992 | Rogers et al. |
| 5,175,273 A | 12/1992 | Bischofberger et al. |
| 5,367,066 A | 11/1994 | Urdea et al. |
| 5,432,272 A | 7/1995 | Benner |
| 5,457,187 A | 10/1995 | Gmelner et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |
| 5,750,692 A | 5/1998 | Cook et al. |
| 5,763,588 A | 6/1998 | Matteucci et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,525,191 B1 | 2/2003 | Ramasamy |
| 6,670,461 B1 | 12/2003 | Wengel et al. |
| 6,770,748 B2 | 8/2004 | Imanishi et al. |
| 6,794,499 B2 | 9/2004 | Wengel et al. |

(Continued)

FOREIGN PATENT DOCUMENTS

| | | |
|---|---|---|
| WO | WO 99/14226 | 3/1999 |
| WO | WO 2004/106356 | 12/2004 |

(Continued)

OTHER PUBLICATIONS

Akinc et al., "A combinatorial library of lipid-like materials for delivery of RNAi therapeutics" Nat. Biotechnol. (2008) 26(5):561-569.

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Alvarez-Garcia et al., "MicroRNA functions in animal development and human disease" Development (2005) 132(21):4653-4662.

(Continued)

*Primary Examiner* — Amy Bowman
(74) *Attorney, Agent, or Firm* — Ionis Pharmaceuticals, Inc. Patent Dept.

(57) ABSTRACT

The present invention provides compounds and methods for competitive modulation of microRNAs. Such compounds and methods have profound effects on cells. MicroRNAs (microRNAs), are small (approximately 18-24 nucleotides in length), non-coding RNA molecules encoded in the genomes of plants and animals. In certain instances, microRNAs regulate the expression of genes by binding to the 3'-untranslated regions (3'-UTR) of specific mRNAs. More than 1000 different microRNAs have been identified in plants and animals.

15 Claims, 33 Drawing Sheets

(56) References Cited

U.S. PATENT DOCUMENTS

| | | | |
|---|---|---|---|
| 7,034,133 | B2 | 4/2006 | Wengel et al. |
| 7,053,207 | B2 | 5/2006 | Wengel |
| 7,399,845 | B2 | 7/2008 | Seth et al. |
| 7,427,672 | B2 | 9/2008 | Imanishi et al. |
| 7,741,457 | B2 | 6/2010 | Seth et al. |
| 2004/0171570 | A1 | 9/2004 | Allerson et al. |
| 2005/0130923 | A1 | 6/2005 | Bhat et al. |
| 2007/0287831 | A1 | 12/2007 | Seth et al. |
| 2008/0039618 | A1 | 2/2008 | Allerson et al. |
| 2010/0267149 | A1 | 10/2010 | Lima et al. |
| 2011/0300155 | A1 | 12/2011 | Chatterjee et al. |

FOREIGN PATENT DOCUMENTS

| | | |
|---|---|---|
| WO | WO 2005/021570 | 3/2005 |
| WO | WO 2007/134181 | 11/2007 |
| WO | WO 2008/042973 | 4/2008 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/100320 | 8/2009 |
| WO | WO 2010/036698 | 4/2010 |
| WO | WO 2011/017521 | 2/2011 |
| WO | WO 2011/138328 | 11/2011 |

OTHER PUBLICATIONS

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.

Bovenschen et al., "NK cell protease granzyme M targets alpha-tubulin and disorganizes the microtubule network" J. Immunol. (2008) 180(12):8184-8191.

Braasch et al., "Locked nucleic acid (LNA): fine-tuning the recognition of DNA and RNA" Chem. Biol. (2001) 8:1-7.

Chatterjee et al., "Active turnover modulates mature microRNA activity in Caenorhabditis elegans" Nature (2009) 461(7263):546-549.

Chekulaeva et al., "Mechanisms of miRNA-mediated post-transcriptional regulation in animal cells" Curr. Opin. Cell Biol. (2009) 21(3):452-560.

Crooke et al., "Pharmacokinetic Properties of Several Novel Oligonucleotide Analogs in mice" J. Pharmacol. Exp. Ther. (1996) 277(2):923-937.

Elayadi et al., "Application of PNA and LNA oligomers to chemotherapy" Curr. Opinion Invens. Drugs (2001) 2:558-561.

Englisch et al., "Chemically Modified Oligonucleotides as Probes and Inhibitors" Agnew Chem. Int. Ed. Engl. (1991) 30:613-629.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

Goping et al., "Identification of {alpha}-tubulin as a granzyme B substrate during CTL-mediated apoptosis" J. Cell Sci. (2006) 119(Pt 5):858-865.

Harris et al., "The microtubule-targeting agent T0070907 induces proteasomal degradation of tubulin" Biochem. Biophys. Res. Comm. (2009) 388(2):345-349.

Huff et al., "Microtubule-disrupting chemotherapeutics result in enhanced proteasome-mediated degradation and disappearance of tubulin in neural cells" Cancer Res. (2010) 70(14):5870-5879.

Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327-330.

Khan et al., "Transfection of small RNAs globally perturbs gene regulation by endogenous microRNAs" Nat. Biotechnol. (2009) 27(6):502-578.

Koller et al., "Competition for RISC binding predicts in vitro potency of siRNA" Nucleic Acids Res. (2006) 34(16):4467-4476.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kumar et al., "The first analogues of LNA (locked nucleic acids): phosphorothioate-LNA and 2'-thio-LNA" Bioorg Med Chem Lett. (1998) 8:2219-2222.

Lee et al., "MicroRNA maturation: stepwise processing and subcellular localization" EMBO J. (2002) 21(17):4663-4670.

Letsinger et al., "Cholesteryl-conjugated oligonucleotides: Synthesis, properties, and activity as inhibitors of replication of human immunodeficiency virus in cell culture" PNAS (1989) 86:6553-6556.

Leumann et al., "DNA Analogues: From Supramolecular Principles to Biological Properties" Bioorganic & Medicinal Chemistry (2002) 10:841-854.

Lima et al., "The Positional Influence of the Helical Geometry of the Heteroduplex Substrate on Human RNase H1 Catalysis" Mol. Pharmacol. (2007) 71:73-82.

Manoharan et al., "Chemical Modifications to Improve Uptake and Bioavailability of Antisense Oligonucleotides" Ann. N.Y. Acad. Sci. (1992) 660: 306-309.

Manoharan et al., "Cholic Acid-Oligonucleotide Conjugates for Antisense Applications" Bioorg. Med. Chem. Lett. (1994) 4:1053-1060.

Manoharan et al., "Introduction of a Lipophilic Thioether Tether in the Minor Groove of Nucleic Acids for Antisense Applications" Bioorg. Med. Chem. Lett. (1993) 3(12):2765-2770.

Manoharan et al., "Lipidic Nucleic Acids" Tetrahedron Lett. (1995) 36(21):3651-3654.

Manoharan et al., "Oligonucleotide Conjugates: Alteration of the Pharmacokinetic Properties of Antisense Agents" Nucleosides & Nucleotides (1995) 14(3-5):969-973.

Mishra et al., "Improved leishmanicidal effect of phosphorotioate antisense oligonucleotides by LDL-mediated delivery" Biochim. Biophys. Acta (1995) 1264:229-237.

Oberhauser et al., "Effective incorporation of 2'-O-methyl-oligoribonucleotides into liposomes and enhanced cell association through modifications with thiocholesterol" Nucl. Acids Res. (1992) 20(3):533-538.

Orum et al., "Locked nucleic acids: A promising molecular family for gene-function analysis and antisense drug development" Curr. Opinion Mol. Ther. (2001) 3:239-243.

Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.

Sanghvi, "Heterocyclic base modifications in nucleic acids and their applications in antisense oligonucleotides" Antisense Research and Applications, Crooke and Lebleu ed., CRC Press (1993) 273-302.

Shea et al., "Synthesis, hybridization properties and antiviral activity of lipid-oligodeoxynucleotide conjugates" Nucl. Acids Res. (1990) 18(13):3777-3783.

Singh et al., "LNA (locked nucleic acids): synthesis and high-affinity nucleic acid recognition" Chem. Commun. (1998) 455-456.

Singh et al., "Synthesis of 2'-amino-LNA: A novel conformationally restricted high-affinity oligonucleotide analogue with a handle" J. Org. Chem. (1998) 63: 10035-10039.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.

Svinarchuk et al., "Inhibition of HIV proliferation in MT-4 cells by antisense oligonucleotide conjugated to lipophilic groups" Biochimie (1993) 75:49-54.

Tagami et al., "Global gene expression profiling in cultured cells is strongly influenced by treatment with siRNA-cationic liposome complexes" Pharm. Res. (2008) 25(11):2497-2504.

(56) References Cited

OTHER PUBLICATIONS

Vickers et al., "Reduced levels of Ago2 expression result in increased siRNA competition in mammalian cells" Nucleic Acids Res. (2007) 35(19):6598-6610.

Wahlestedt et al., "Potent and nontoxic antisense oligonucleotide containing locked nucleic acids" Proc. Natl. Acad. Sci. USA (2000) 97: 5633-5638.

Wang et al., "Export of microRNAs and microRNA-protective protein by mammalian cells" Nucleic Acids Res. (2010) 38(20):1-12.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

Effect of various siRNAs on α-tubulin protein expression

Quantification of α-tubulin levels normalized to hnRNP A2 in siRNA-treated cells Dose-dependent effect of siRNA on α-tubulin protein level

Dose-dependent effect of siRNA on target protein levels

Quantification of protein levels in siRNA (HSS176903) treated HeLa cells normalized to γ-tubulin Effect of siRNA on α-tubulin levels when used alone or in combination with other siRNAs Quantification of α-tubulin levels in siRNA treated HeLa cells when used alone or in combination with other siRNAs normalized to GAPDH Effect of various siRNAs on α-tubulin level in MHT cells Quantification of α-tubulin level in siRNA treated MHT cells

Ago2 effect on siRNA-induced α-tubulin reduction

RT-PCR of co-immunoprecipitated siRNA, ISIS 341401, with various proteins

Tubulin does not co-immunoprecipitate with siRNA, ISIS 341401

Effect of various siRNAs on endogenous miRNA levels

Quantification of endogenous miRNA levels normalized to U16 snoRNA

Effect of siRNA transfection on miR-21 levels

Quantification of miR-21 normalized to U2 snRNA in siRNA treated cells

Dose-dependent effect of siRNA, Isis 341401, on endogenous miRNA levels

Quantification of miRNA levels normalized to U16 snoRNA

Dose-dependent effect of siRNA, s14431, on endogenous miRNA levels in HeLa cells Quantification of miRNA levels normalized to U16 snoRNA miRNA levels at various time points after siRNA transfection Levels of miRNA co-immunoprecipitated with Ago-2 following siRNA transfection

Levels of transfected siRNA, Isis 341401, co-immunoprecipitated with Ago2 following transfection

Effect of siRNA, Isis 341401, on Ago2 protein level

Schematic depiction of miRNAs potentially targeting GZMB 3' UTR region

1. miR-520a-5p
   miR-525-5p
2. miR-378
3. miR-422a
4. miR-199b-5p
   miR-150
5. miR-199a-5p
6. miR-202
7. miR-512 miR-378 and miR-422a levels in siRNA-treated HeLa cells

Effect of Fen1 siRNA on GZMB mRNA level

Schematic depiction of miRNAs potentially targeting GZMM 3' UTR region

1. miR-615-5p
2. miR-331-3p
3. miR-1247
4. miR-1260
   miR-1280
5. miR-1224-3p
6. miR-532-3p
   miR-339-39
   miR-1274
7. miR-133a
   miR-133b

Effect of Fen1 siRNA transfection on miRNA levels in HeLa cells

GZMM mRNA levels in siRNA transfected cells

GZMM and tubulin protein levels in siRNA transfected cells

Role of GZMB and GZMM on Fen1 siRNA-induced tubulin reduction

Role of GZMB and GZMM on Fen1 siRNA-induced tubulin reduction

SEQUENCE LISTING

<160> NUMBER OF SEQ ID NOS: 65

<210> SEQ ID NO 1
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 1
aactatacaa cctactacct ca                                              22

<210> SEQ ID NO 2
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 2
cgccaatatt tacgtgctgc ta                                              22

<210> SEQ ID NO 3
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 3
ctacctgcac tgtaagcact ttg                                             23

<210> SEQ ID NO 4
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 4

```
tcagttttgc atggatttgc aca                                              23

<210> SEQ ID NO 5
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 5
tcaacatcag tctgataagc ta                                               22

<210> SEQ ID NO 6
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 6
ctgttcctgc tgaactgagc ca                                               22

<210> SEQ ID NO 7
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 7
gcggaactta gccactgtga a                                                21

<210> SEQ ID NO 8
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 8
acaggccggg acaagtgcaa ta                                               22

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
ttgctcagta agaattttcg                                                  20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
aataccaggt cgatgcgtgg                                                  20

<210> SEQ ID NO 11
<211> LENGTH: 21
<212> TYPE: DNA
```

```
<213> ORGANISM: Artificial sequence
<220> FEATURE:
<223> OTHER INFORMATION: Primer

<400> SEQUENCE: 11
gtgaaactgg tgctggaaaa c                                              21

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
cagcatcctc tttcccagtg                                                20

<210> SEQ ID NO 13
<211> LENGTH: 24
<212> TYPE: DNA
<213> ORGANISM: Artificial sequence
<220> FEATURE:
<223> OTHER INFORMATION: Probe

<400> SEQUENCE: 13
aaatggccca taccgacagc tctt                                           24

<210> SEQ ID NO 14
<211> LENGTH: 20
<212> TYPE: DNA
<213> ORGANISM: Artificial sequence
<220> FEATURE:
<223> OTHER INFORMATION: Primer

<400> SEQUENCE: 14
gggatgggtc ttttcacagg                                                20

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
cggtggcttc ctgatacaag                                                20

<210> SEQ ID NO 16
<211> LENGTH: 23
<212> TYPE: DNA
<213> ORGANISM: Artificial sequence
<220> FEATURE:
<223> OTHER INFORMATION: Probe

<400> SEQUENCE: 16
ctgggtcggc tcctgttctt tga                                            23

<210> SEQ ID NO 17
<211> LENGTH: 24
<212> TYPE: DNA
<213> ORGANISM: Artificial sequence
<220> FEATURE:
<223> OTHER INFORMATION: Primer

<400> SEQUENCE: 17
gcatgtgtaa caacagccgc ttct                                           24
```

-continued

```
<210> SEQ ID NO 18
<211> LENGTH: 24
<212> TYPE: DNA
<213> ORGANISM: Artificial sequence
<220> FEATURE:
<223> OTHER INFORMATION: Primer

<400> SEQUENCE: 18
ttgaagatgt cagtgcagac cctg                                            24

<210> SEQ ID NO 19
<211> LENGTH: 24
<212> TYPE: DNA
<213> ORGANISM: Artificial sequence
<220> FEATURE:
<223> OTHER INFORMATION: Probe

<400> SEQUENCE: 19
tgttggccgg agtcctgtcc ttca                                            24

<210> SEQ ID NO 20
<211> LENGTH: 20
<212> TYPE: DNA
<213> ORGANISM: Artificial sequence
<220> FEATURE:
<223> OTHER INFORMATION: Primer

<400> SEQUENCE: 20
atggtgtgga tgtggaagtc                                                 20

<210> SEQ ID NO 21
<211> LENGTH: 20
<212> TYPE: DNA
<213> ORGANISM: Artificial sequence
<220> FEATURE:
<223> OTHER INFORMATION: Primer

<400> SEQUENCE: 21
agagtgggaa gaggtgagtg                                                 20

<210> SEQ ID NO 22
<211> LENGTH: 23
<212> TYPE: DNA
<213> ORGANISM: Artificial sequence
<220> FEATURE:
<223> OTHER INFORMATION: Probe

<400> SEQUENCE: 22
ttgaaccgca aagaggtgct gac                                             23

<210> SEQ ID NO 23
<211> LENGTH: 16
<212> TYPE: DNA
<213> ORGANISM: Artificial sequence
<220> FEATURE:
<223> OTHER INFORMATION: Primer

<400> SEQUENCE: 23
gggccgcctg gatgat                                                     16

<210> SEQ ID NO 24
<211> LENGTH: 18
<212> TYPE: DNA
<213> ORGANISM: Artificial sequence
<220> FEATURE:
```

<223> OTHER INFORMATION: Primer

<400> SEQUENCE: 24
tggctccttg cgcttagc                                                    18

<210> SEQ ID NO 25
<211> LENGTH: 28
<212> TYPE: DNA
<213> ORGANISM: Artificial sequence
<220> FEATURE:
<223> OTHER INFORMATION: Probe

<400> SEQUENCE: 25
tcttcaaggt gaccggctca ctctcttc                                         28

<210> SEQ ID NO 26
<211> LENGTH: 23
<212> TYPE: DNA
<213> ORGANISM: Artificial sequence
<220> FEATURE:
<223> OTHER INFORMATION: Primer

<400> SEQUENCE: 26
ccacttactg atactcctga cac                                              23

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
caggaacacc atagccagag                                                  20

<210> SEQ ID NO 28
<211> LENGTH: 24
<212> TYPE: DNA
<213> ORGANISM: Artificial sequence
<220> FEATURE:
<223> OTHER INFORMATION: Probe

<400> SEQUENCE: 28
tgctttgaga gccagatgtg gagg                                             24

<210> SEQ ID NO 29
<211> LENGTH: 19
<212> TYPE: DNA
<213> ORGANISM: Artificial sequence
<220> FEATURE:
<223> OTHER INFORMATION: Primer

<400> SEQUENCE: 29
aaaagagttc ccacagccc                                                   19

<210> SEQ ID NO 30
<211> LENGTH: 21
<212> TYPE: DNA
<213> ORGANISM: Artificial sequence
<220> FEATURE:
<223> OTHER INFORMATION: Primer

<400> SEQUENCE: 30
ggccatttta tgtgcagtgt g                                                21

<210> SEQ ID NO 31
<211> LENGTH: 23
<212> TYPE: DNA
<213> ORGANISM: Artificial sequence
<220> FEATURE:
<223> OTHER INFORMATION: Probe

<400> SEQUENCE: 31
agtgtgattg gaagagccct cgg                                    23

<210> SEQ ID NO 32
<211> LENGTH: 23
<212> TYPE: DNA
<213> ORGANISM: Artificial sequence
<220> FEATURE:
<223> OTHER INFORMATION: Primer

<400> SEQUENCE: 32
gaaagaggaa aaggatctgc ttg                                    23

<210> SEQ ID NO 33
<211> LENGTH: 21
<212> TYPE: DNA
<213> ORGANISM: Artificial sequence
<220> FEATURE:
<223> OTHER INFORMATION: Primer

<400> SEQUENCE: 33
accgatctgg agacgaattt g                                      21

<210> SEQ ID NO 34
<211> LENGTH: 25
<212> TYPE: DNA
<213> ORGANISM: Artificial sequence
<220> FEATURE:
<223> OTHER INFORMATION: Probe

<400> SEQUENCE: 34
ttaccactgc cacaagattc tgccc                                  25

<210> SEQ ID NO 35
<211> LENGTH: 27
<212> TYPE: DNA
<213> ORGANISM: Artificial sequence
<220> FEATURE:
<223> OTHER INFORMATION: Primer

<400> SEQUENCE: 35
cctgtactta ctggtgtgga aaatagc                                27

<210> SEQ ID NO 36
<211> LENGTH: 20
<212> TYPE: DNA
<213> ORGANISM: Artificial sequence
<220> FEATURE:
<223> OTHER INFORMATION: Primer

<400> SEQUENCE: 36
ccgtgtgaaa gacgcatctg                                        20

<210> SEQ ID NO 37
<211> LENGTH: 26
<212> TYPE: DNA
<213> ORGANISM: Artificial sequence
<220> FEATURE:
<223> OTHER INFORMATION: Probe -continued

```
<400> SEQUENCE: 37
tgcaggtagg accattgcag tgatgg                                          26

<210> SEQ ID NO 38
<211> LENGTH: 20
<212> TYPE: DNA
<213> ORGANISM: Artificial sequence
<220> FEATURE:
<223> OTHER INFORMATION: Primer

<400> SEQUENCE: 38
tcctcaatga agggtcccaa                                                 20

<210> SEQ ID NO 39
<211> LENGTH: 19
<212> TYPE: DNA
<213> ORGANISM: Artificial sequence
<220> FEATURE:
<223> OTHER INFORMATION: Primer

<400> SEQUENCE: 39
gccgcgttcc aggaaatat                                                  19

<210> SEQ ID NO 40
<211> LENGTH: 21
<212> TYPE: DNA
<213> ORGANISM: Artificial sequence
<220> FEATURE:
<223> OTHER INFORMATION: Probe

<400> SEQUENCE: 40
cccgtccccg ttcttcccac c                                               21

<210> SEQ ID NO 41
<211> LENGTH: 26
<212> TYPE: DNA
<213> ORGANISM: Artificial sequence
<220> FEATURE:
<223> OTHER INFORMATION: Primer

<400> SEQUENCE: 41
aatggctaag tgaagatgac aatcat                                          26

<210> SEQ ID NO 42
<211> LENGTH: 25
<212> TYPE: DNA
<213> ORGANISM: Artificial sequence
<220> FEATURE:
<223> OTHER INFORMATION: Primer

<400> SEQUENCE: 42
tgcacatatc attacaccag ttcgt                                           25

<210> SEQ ID NO 43
<211> LENGTH: 30
<212> TYPE: DNA
<213> ORGANISM: Artificial sequence
<220> FEATURE:
<223> OTHER INFORMATION: Probe

<400> SEQUENCE: 43
ttgcagcaat tcactgtaaa gctggaaagg                                      30

<210> SEQ ID NO 44
<211> LENGTH: 19
```

<212> TYPE: RNA
<213> ORGANISM: Artificial sequence
<220> FEATURE:
<223> OTHER INFORMATION: Synthetic oligonucleotide

<400> SEQUENCE: 44
aaguaaggac cagagacaa                                                    19

<210> SEQ ID NO 45
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 45
uugucucugg uccuuacuu                                                    19

<210> SEQ ID NO 46
<211> LENGTH: 19
<212> TYPE: DNA
<213> ORGANISM: Artificial sequence
<220> FEATURE:
<223> OTHER INFORMATION: Primer

<400> SEQUENCE: 46
ccgcatgcaa atcaaccat                                                    19

<210> SEQ ID NO 47
<211> LENGTH: 21
<212> TYPE: DNA
<213> ORGANISM: Artificial sequence
<220> FEATURE:
<223> OTHER INFORMATION: Primer

<400> SEQUENCE: 47
gctacctcgg aagcaccttt c                                                 21

<210> SEQ ID NO 48
<211> LENGTH: 28
<212> TYPE: DNA
<213> ORGANISM: Artificial sequence
<220> FEATURE:
<223> OTHER INFORMATION: Probe

<400> SEQUENCE: 48
ccattgacat catctgtggg ttcctgaa                                          28

<210> SEQ ID NO 49
<211> LENGTH: 23
<212> TYPE: DNA
<213> ORGANISM: Artificial sequence
<220> FEATURE:
<223> OTHER INFORMATION: Primer

<400> SEQUENCE: 49
cttgcaatga tgtcgtaatt tgc                                               23

<210> SEQ ID NO 50
<211> LENGTH: 23
<212> TYPE: DNA
<213> ORGANISM: Artificial sequence
<220> FEATURE:
<223> OTHER INFORMATION: Primer

<400> SEQUENCE: 50
tcgtcaacct tctgtaccag ctt                                          23

<210> SEQ ID NO 51
<211> LENGTH: 29
<212> TYPE: DNA
<213> ORGANISM: Artificial sequence
<220> FEATURE:
<223> OTHER INFORMATION: Probe

<400> SEQUENCE: 51
ttactctgtt ctcagcgaca gttgcctgc                                    29

<210> SEQ ID NO 52
<211> LENGTH: 21
<212> TYPE: DNA
<213> ORGANISM: Artificial sequence
<220> FEATURE:
<223> OTHER INFORMATION: Primer

<400> SEQUENCE: 52
gcttggcttc ttctggactc a                                            21

<210> SEQ ID NO 53
<211> LENGTH: 18
<212> TYPE: DNA
<213> ORGANISM: Artificial sequence
<220> FEATURE:
<223> OTHER INFORMATION: Primer

<400> SEQUENCE: 53
tcgcgagctt caccatga                                                18

<210> SEQ ID NO 54
<211> LENGTH: 24
<212> TYPE: DNA
<213> ORGANISM: Artificial sequence
<220> FEATURE:
<223> OTHER INFORMATION: Probe

<400> SEQUENCE: 54
cgccacttgt ccgcttcaca ctcc                                         24

<210> SEQ ID NO 55
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA

<400> SEQUENCE: 55
gaguguaaca ucguaguaat t                                            21

<210> SEQ ID NO 56
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA

<400> SEQUENCE: 56
ggaccauaga uguuaccgat t                                              21

<210> SEQ ID NO 57
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA

<400> SEQUENCE: 57
caguguuagu cauaucguat t                                              21

<210> SEQ ID NO 58
<211> LENGTH: 19
<212> TYPE: RNA
<213> ORGANISM: Artificial sequence
<220> FEATURE:
<223> OTHER INFORMATION: Synthetic oligonucleotide

<400> SEQUENCE: 58
aaguaaggac cagagacaa                                                 19

<210> SEQ ID NO 59
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 59
caggaacagu uuguggaucu gugca                                          25

<210> SEQ ID NO 60
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 60
caucaagccc guguaugucu uugau                                          25

<210> SEQ ID NO 61
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA

<400> SEQUENCE: 61
gaagugaagu uguacaagat t                                              21

<210> SEQ ID NO 62
<211> LENGTH: 21
<212> TYPE: DNA
<213> ORGANISM: Artificial sequence
<220> FEATURE:
<223> OTHER INFORMATION: Synthetic oligonucleotide
<220> FEATURE:

```
<221> NAME/KEY: misc_feature
<222> LOCATION: (1)..(19)
<223> OTHER INFORMATION: bases at these positions are RNA

<400> SEQUENCE: 62
gaagtaaagc tctacaagat t                                            21

<210> SEQ ID NO 63
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 63
ggcaacuguc gcugagaaca                                              20

<210> SEQ ID NO 64
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 64
ccuacauggc uuaucuuaug aucug                                        25

<210> SEQ ID NO 65
<211> LENGTH: 25
<212> TYPE: RNA
<213> ORGANISM: Artificial sequence
<220> FEATURE:
<223> OTHER INFORMATION: Synthetic oligonucleotide

<400> SEQUENCE: 65
cagccaucca gcacccucgc uacaa                                        25
```

COMPETITIVE MODULATION OF MICRORNAS

FIELD OF THE INVENTION

The present invention pertains generally to chemically-modified oligonucleotides for use in research, diagnostics, and/or therapeutics.

SEQUENCE LISTING

The present application is being filed along with a Sequence Listing in electronic format. The Sequence Listing is provided as a file entitled CORE0102USASEQ_ST25.txt, created Jun. 9, 2015, which is 16 Kb in size. The information in the electronic format of the sequence listing is incorporated herein by reference in its entirety.

BACKGROUND OF THE INVENTION

MicroRNAs (microRNAs), are small (approximately 18-24 nucleotides in length), non-coding RNA molecules encoded in the genomes of plants and animals. In certain instances, microRNAs regulate the expression of genes by binding to the 3'-untranslated regions (3'-UTR) of specific mRNAs. More than 1000 different microRNAs have been identified in plants and animals. Certain mature microRNAs appear to originate from long endogenous primary microRNA transcripts (also known as pri-microRNAs, pri-mirs, pri-miRs or pri-pre-microRNAs) that are often hundreds of nucleotides in length (Lee, et al., EMBO J., 2002, 21(17), 4663-4670).

Functional analyses of microRNAs have revealed that these small non-coding RNAs contribute to different physiological processes in animals, including developmental timing, organogenesis, differentiation, patterning, embryogenesis, growth control and programmed cell death. Examples of particular processes in which microRNAs participate include stem cell differentiation, neurogenesis, angiogenesis, hematopoiesis, and exocytosis (reviewed by Alvarez-Garcia and Miska, Development, 2005, 132, 4653-4662).

SUMMARY OF THE INVENTION

In certain embodiments, the present invention provides methods for identifying competitive microRNA modulating compounds. Such methods comprising performing an assay to determine whether a test compound is capable of competing with at least one microRNA for a microRNA-associated protein. In certain embodiments, the microRNA-associated protein is required for microRNA activity. In certain embodiments, the microRNA-associated protein is Ago2. In certain embodiments, the microRNA-associated protein is involved in the inactivation, degradation, and/or export of the microRNA. In certain embodiments, the microRNA-associated protein is nucleolin. In certain embodiments, the microRNA-associated protein is nucleophosmin. In certain embodiments, the modulation is a decrease in the activity of at least one microRNA in the cell. In certain embodiments, the modulation is an increase in the amount and/or activity of at least one microRNA in the cell.

Certain such competitive microRNA modulators compete selectively for a microRNA-associated protein with one or more microRNA, but do not compete or compete to a lesser degree with at least one other microRNA. Certain such selective competitive microRNA modulators may be identified and used to modulate specific microRNAs. In certain embodiments, competitive microRNA modulators compete for a microRNA-associated protein with more than one microRNA, with more than 10 microRNAs, with at least half of the microRNAs in the cell; with essentially all of the microRNAs in the cell; or with all of the microRNAs in the cell. Such broad competitive microRNA modulators may be identified and used to affect the overall microRNA activity or amount (or miR-tone) in the cell.

In certain embodiments, competitive microRNA modulators are small molecules. In certain embodiments, competitive microRNA modulators are oligomers, such as oligonucleotides. In certain such embodiments, microRNA modulators are double-stranded oligonucleotides. Certain such oligonucleotides comprise at least one RNA or RNA-like nucleoside.

Since competitive microRNA modulators derive their activity from the ability to competitively bind microRNA-associated proteins (and thus displace microRNAs), and not from hybridization, in certain embodiments, competitive microRNA modulators have a nucleobase sequence that is not complementary to any target nucleic acid in the cell. Alternatively, certain competitive microRNA modulators are complementary to a target nucleic acid. Certain such competitive microRNA modulators may exert activity by competing for a microRNA-associated protein and also have hybridization-based antisense activity. Certain such competitive microRNA modulators are siRNA compounds.

In certain embodiments, competitive microRNA modulators modulate the activity and/or amount of one or more microRNA in a cell and consequently alter the expression of one or more object mRNA of the modulated microRNA. In certain instances, the object mRNA or its associated protein is associated with a disease or disorder. In certain embodiments, competitive microRNA modulators ultimately modulate the expression of function of such mRNA to alleviate one or more symptom of the disease or disorder.

In certain embodiments, methods and compounds described herein are useful in vitro. In certain embodiments such methods and compounds are used in diagnostics and/or for target validation experiments.

DETAILED DESCRIPTION OF THE INVENTION

Figure 1:
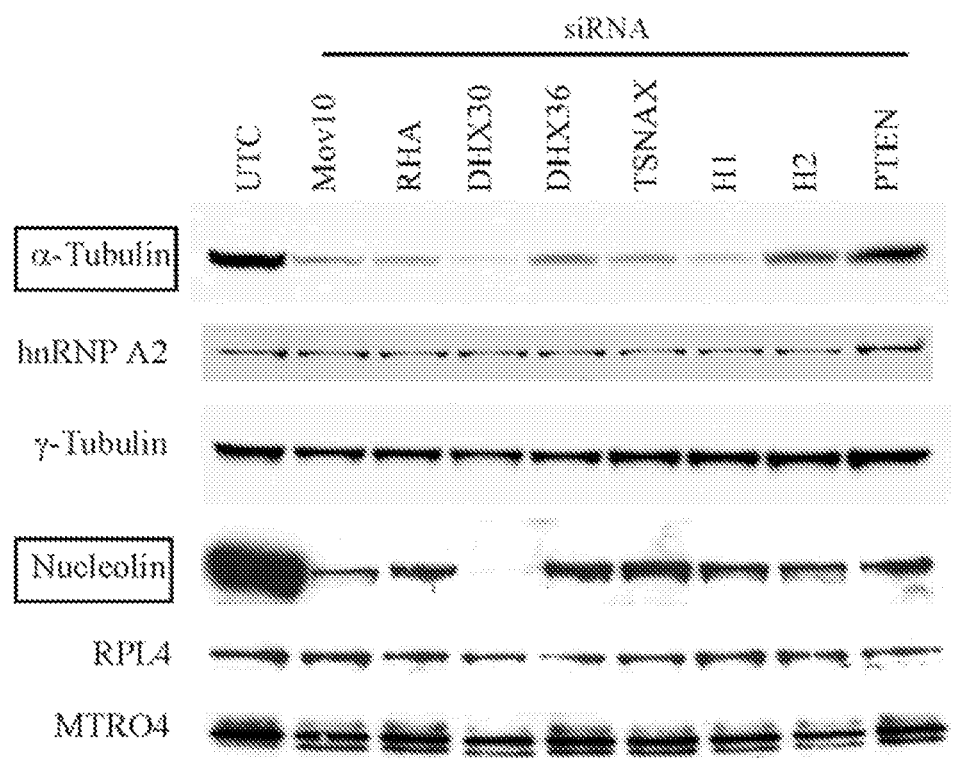
FIG. 1 shows a western blot illustrating relative protein expression of various proteins following treatment of HeLa cells with various siRNAs.

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. DEFINITIONS

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluoroine at the 2' position. Unless otherwise indicated, the fluorine in a 2'-F nucleoside is in the ribo position (replacing the OH of a natural ribose).

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "RNA-like nucleoside" means a modified nucleoside that adopts a northern configuration and functions like RNA when incorporated into an oligonucleotide. RNA-like nucleosides include, but are not limited to 3'-endo furanosyl nucleosides and RNA surrogates.

As used herein, "3'-endo-furanosyl nucleoside" means an RNA-like nucleoside that comprises a substituted sugar moiety that has a 3'-endo conformation. 3'-endo-furanosyl nucleosides include, but are not limited to: 2'-MOE, 2'-F, 2'-OMe, LNA, ENA, and cEt nucleosides.

As used herein, "RNA-surrogate nucleoside" means an RNA-like nucleoside that does not comprise a furanosyl. RNA-surrogate nucleosides include, but are not limited to hexitols and cyclopentanes.

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measurable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "mRNA" means an RNA molecule that encodes a protein.

As used herein, "pre-mRNA" means an RNA transcript that has not been fully processed into mRNA. Pre-RNA includes one or more intron.

As used herein, "object RNA" means an RNA molecule other than a target RNA, the amount, activity, splicing, and/or function of which is modulated, either directly or indirectly, by a target nucleic acid. In certain embodiments, a target nucleic acid modulates splicing of an object RNA. In certain such embodiments, an antisense compound modulates the amount or activity of the target nucleic acid, resulting in a change in the splicing of an object RNA and ultimately resulting in a change in the activity or function of the object RNA.

As used herein, "microRNA" means a naturally occurring, small, non-coding RNA that represses gene expression of at least one mRNA. In certain embodiments, a microRNA represses gene expression by binding to a target site within a 3' untranslated region of an mRNA. In certain embodiments, a microRNA has a nucleobase sequence as set forth in miRBase, a database of published microRNA sequences found at http://microrna.sanger.ac.uk/sequences/. In certain embodiments, a microRNA has a nucleobase sequence as set forth in miRBase version 18.0 released November 2011, which is herein incorporated by reference in its entirety.

As used herein, "microRNA mimic" means an oligomeric compound having a sequence that is at least partially identical to that of a microRNA. In certain embodiments, a microRNA mimic comprises the microRNA seed region of a microRNA. In certain embodiments, a microRNA mimic modulates translation of more than one target nucleic acids. In certain embodiments, a microRNA mimic is double-stranded.

As used herein, "microRNA-associated protein" means a protein that interacts directly with a microRNA. In certain embodiments, a miroRNA-associated protein is Ago2. In certain embodiments, a microRNA-associated protein is nucleolin. In certain embodiments, a microRNA-associated protein is nucleophosmin.

As used herein, "competitive microRNA modulating compound" means a compound capable of competively modulating the activity and/or amount of at least one target microRNA in a cell, without interacting directly with the target microRNA and instead by interacting with a microRNA-associated protein. In certain embodiments, a competitive microRNA modulating compound is an oligomer. In certain embodiments, a competitive microRNA modulating compound is an oligonucleotide. In certain embodiments, a competitive microRNA modulating compound is single-stranded. In certain embodiments, a competitive microRNA modulating compound is double-stranded.

As used herein, "selective competitive microRNA modulating compound" means a compound capable of competing for a microRNA-associated protein by modulating the activity and/or amount of at least one target microRNA in a cell and not capable of modulating, or modulating to a substantially lower degree, the amount and/or activity of at least one other (non-target) microRNA in the cell and without interacting directly with the target microRNA. In certain embodiments, a selective competitive microRNA modulating compound is an oligomer. In certain embodiments, a selective competitive microRNA modulating compound is an oligonucleotide. In certain embodiments, a selective competitive microRNA modulating compound is single-stranded. In certain embodiments, a selective competitive microRNA modulating compound is double-stranded.

As used herein, "broad competitive microRNA modulating compound" means a compound capable of modulating the activity and/or amount of more than one microRNA in a cell without interacting directly with the target microRNAs. In certain embodiments, a broad competitive microRNA modulating compound is capable of modulating the activity and/or amount of more than two, three, four or five microRNAs in a cell. In certain embodiments, a broad competitive microRNA modulating compound is capable of modulating the activity and/or amount of more than 50%, 60%, 70%, or 80% of the total microRNAs in a cell. In certain embodiments, a broad competitive microRNA modulating compound is an oligomer. In certain embodiments, a broad competitive microRNA modulating compound is an oligonucleotide. In certain embodiments, a broad competitive microRNA modulating compound is single-stranded. In certain embodiments, a broad competitive microRNA modulating compound is double-stranded.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "modification motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substuent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)R$_{aa}$), carboxyl (—C(O)O—R$_{aa}$), aliphatic groups, alicyclic groups, alkoxy, substituted oxy (—O—R$_{aa}$), aryl, aralkyl, heterocyclic radical, heteroaryl, heteroarylalkyl, amino (—N(R$_{bb}$)(R$_{cc}$)), imino (=NR$_{bb}$), amido (—C(O)N(R$_{bb}$)(R$_{cc}$) or —N(R$_{bb}$)C(O)R$_{aa}$), azido (—N$_3$), nitro (—NO$_2$), cyano (—CN), carbamido (—OC(O)N(R$_{bb}$)(R$_{cc}$) or —N(R$_{bb}$)C(O)OR$_{aa}$), ureido (—N(R$_{bb}$)C(O)N(R$_{bb}$)(R$_{cc}$)), thioureido (—N(R$_{bb}$)C(S)N(R$_{bb}$)—(R$_{cc}$)), guanidinyl (—N(R$_{bb}$)C(=NR$_{bb}$)N(R$_{bb}$)(R$_{cc}$)), amidinyl (—C(=NR$_{bb}$)N(R$_{bb}$)(R$_{cc}$) or —N(R$_{bb}$)C(=NR$_{bb}$)(R$_{aa}$)), thiol (—SR$_{bb}$), sulfinyl (—S(O)R$_{bb}$), sulfonyl (—S(O)$_2$R$_{bb}$) and sulfonamidyl (—S(O)$_2$N(R$_{bb}$)(R$_{cc}$) or —N(R$_{bb}$)S—(O)$_2$R$_{bb}$). Wherein each R$_{aa}$, R$_{bb}$ and R$_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

B. RNA INTERFERENCE

RNA interference (RNAi) is a process by which double-stranded (dsRNA) triggers specific degradation of homologous mRNAs. RNAi is mediated by small interfering RNAs (siRNAs), 21-24 nts double stranded RNAs (dsRNAs) that are either transfected as in vitro synthesized form, or expressed in cells as long dsRNAs or small hairpin RNAs (shRNAs) that are processed into siRNAs using endogenous proteins including Dicer. The double stranded siRNAs are incorporated into the RNA induced silencing complex (RISC), which includes Ago2. The passenger strand siRNA is then released, and the guide strand siRNA remains associated with Ago2 and directs the RISC to substrate mRNA, which is cleaved by Ago2, resulting in sequence-specific mRNA cleavage through perfect base-pairing of siRNAs with target mRNAs.

MicroRNAs are endogenously expressed small RNAs that mainly function in regulating gene expression through imperfect base-pairing with target mRNAs, either by inhibiting target mRNA translation or by modulating mRNA stability. Since microRNA:mRNA base-pairing involves only short seed sequence, a single microRNA can target multiple microRNAs and a single mRNA can be targeted by multiple microRNAs, making a huge, complex microRNA regulation network. Indeed, it was proposed that more than half of the human genes can be targeted by microRNAs.

siRNA and microRNAs utilize overlapping cellular machinery for biogenesis and function. For example, both siRNA and microRNA associate with Ago2 protein in mammals, the core component of the RISC complex. It has been demonstrated that siRNA and microRNAs can be functionally inter-changeable by altering the base-pairing patterns with mRNA targets. Thus, siRNA can lead to mis-regulation of other non-target genes by functioning as microRNAs through imperfect base-pairing, or by inducing non-specific mRNA cleavage via near-perfect base-pairing, leading to RISC dependent off-target effects. Thus, RNAi is commonly used as a convenient tool for gene functionalization in different model systems.

C. COMPETITIVE MICRORNA MODULATION AND ASSAYS

In certain embodiments, the present invention provides compounds and methods for competitive microRNA modulation. In certain embodiments, the invention provides methods for identifying compounds that modulate the amount and/or activity of one or more microRNA in a cell. In certain instances, microRNAs interact with proteins (microRNA-associated proteins). Such protein interactions result in microRNA activity or in microRNA inactivation, degradation, or export. Compounds that compete with microRNAs for such proteins can modulate the activity and/or amount of one or more microRNA in a cell.

MicroRNAs interact with various microRNA-associated proteins. For example, microRNAs interact with members of the RISC (RNA-induced silencing complex) pathway to suppress translation of one or more messenger RNAs ("object mRNAs"). Ago2 (also known in the art as Argonaute 2 and EIF2C2) is an essential protein of the RISC pathway. In certain instances, Ago2 binds to a microRNA, which in turn hybridizes with a region of an object mRNA that is at least partially complementary to a portion of the microRNA. Formation of an Ago2/microRNA/mRNA complex typically results in reduced or suppressed translation of the object mRNA and thus reduction of the protein encoded by the mRNA ("object protein"). Certain other proteins have been shown or suggested to be involved in inactivation, degradation, and/or export of microRNAs. Such proteins include, but are not limited to nucleophosmin and nucleolin. It has been shown that XRN2, the orthologue of the yeast 5'→3' exoribonuclease Rat1p, is involved in RNA processing and degradation. XRN2 mediates miRNA turn over in nematodes, and that degradation of miRNAs can affect functional miRNA homeostasis. For example, in XRN-2-dependent miRNA turnover in larval lysates. Although Argonaute: miRNA complexes are highly resistant to salt, larval lysate promotes efficient release of the miRNA, exposing it to degradation by XRN-2 (Chatterjee et al., Nature, 2009, 461, 546-549). Disruption of these interactions between microRNAs and microRNA-associated proteins alters the activity and/or amount of microRNAs.

In certain embodiments, competitive microRNA modulators compete with one or more microRNA for binding with at least one microRNA-associated protein. In certain embodiments, competitive microRNA modulators compete with one or more microRNA for Ago2 binding. Such competition results in a reduction in the activity of the microRNA, which leads to de-repression of object mRNA and thus, an increase in expression of object protein. In certain embodiments, the invention provides methods of identifying such competitive microRNA modulators by performing a competition assay using a test compound, a microRNA and Ago2. In certain embodiments, competitive microRNA modulators compete with one or more microRNA for binding with at least one microRNA-associated protein responsible for degradation or export of a microRNA. Such competition results in a decrease in microRNA inactivation, degradation and/or export from the cell. Consequently, microRNA activity will increase and expression of object protein will decrease.

Certain compounds that bind to directly to microRNAs to modulate their activity have been reported. For example, antisense oligonucleotides complementary to a particular target microRNA have been demonstrated to reduce the amount or activity of that target microRNA, resulting in de-repression (increase) in expression of object mRNA otherwise suppressed by that target microRNA. In certain instances, such target microRNA have multiple object mRNA and object proteins. Modulation of a single microRNA, for example by antisense oligonucleotides, has been shown to modulate expression of multiple object proteins.

Certain of the present methods and compounds differ from previously reported anti-microRNA antisense oligonucleotides that specifically hybridize with a particular target microRNA. Certain embodiments of the present invention focus instead on compounds that compete with microRNAs for their associated proteins. In certain embodiments, the invention provides methods for identifying compounds that bind to Ago2 to block or displace binding by one or more microRNA. Since the Ago2/microRNA association is necessary for microRNA mediated activity, compounds that compete with a microRNA for Ago2 reduce such activity of the microRNA. Such compounds capable of competing with microRNAs for Ago2 (competitive microRNA modulators) may have any of a variety of structures. For example, in certain embodiments, competitive microRNA modulators are selected from small molecules and oligomeric compounds, including, but not limited to single- or double-stranded oligonucleotides. Competitive microRNA modulators that are oligomers may also have antisense activity. For example, a double-stranded oligonucleotide may have the duel functions of competing with microRNAs for Ago2 and, by virtue of its nucleobase sequence, may also have antisense activity (e.g., may be an siRNA), and thus directly silences expression of a target nucleic acid as well.

In certain embodiments, competitive microRNA modulators are not complementary to a target mRNA and thus, do not have siRNA activity.

In certain embodiments, competition assays are employed for identifying completive microRNA modulators. Such assays are designed to determine whether a test compound is capable of competing with at least one microRNA for a microRNA-associated protein.

In certain embodiments, assays are performed to determine the ability of a test compound to compete with a microRNA for binding to a microRNA-associated protein (e.g., Ago2). In certain such embodiments, the ability to compete is assessed in a cell. For example, in certain such embodiments, a test compound is contacted with a cell to allow it to interact with a microRNA-associated protein inside the cell; the microRNA-associated protein is then precipitated from the cell and binding of the test compound with the microRNA-associated protein is assessed. In certain embodiments, the ability of a test compound to compete with a microRNA for a microRNA-associated protein is assessed in a cell-free assay. In certain such embodiments, a microRNA-associated protein is contacted with a test compound in the presence of at least one microRNA. In certain embodiments, the concentrations of the test compound, the microRNA, and/or the microRNA-associated protein are varied.

In certain such embodiments, (1) cells or microRNA-associated protein is placed in a multiwell plate; (2) one or more microRNAs is added to each well at the same concentration per well; (3) a test compound is added to each of several wells, typically at several different concentrations; and (4) microRNA-associated protein activity or binding of either the microRNA or the test compound or both is detected and/or measured. Such assays are useful for assessing the relative binding of the test compound compared to the one or more microRNA. In certain embodiments, the concentration of the one or more microRNA is varied and the concentration of the test compound is the same for each well. One of ordinary skill in the art will readily appreciate that these components can be manipulated in a variety of ways. Certain competition assays have been described previously. See e.g., Koller et al., Nucleic Acid Research, 34:16, 4467-4476 (2006), which is hereby incorporated by reference in its entirety.

In certain embodiments, the test compound is a small molecule. In certain embodiments, the test compound is an oligomeric compound. In certain embodiments, the test compound comprises an oligonucleotide. In certain embodiments, the test compound comprises a single-stranded oligonucleotide. In certain embodiments, the test compound comprises a double-stranded oligonucleotide. In certain embodiments, the test compound comprises a single- or double-stranded oligonucleotide and at least one conjugate. In certain embodiments, the test compound comprises an antisense oligonucleotide.

In certain embodiments, the microRNA-associated protein is a RISC protein. In certain embodiments, the microRNA-associated protein is an Ago protein. In certain embodiments, the microRNA associate protein is Ago2. In certain embodiments, the certain embodiments, the microRNA-associated protein is a protein that reduced the activity or amount of a microRNA in a cell. In certain embodiments, the microRNA-associated protein degrades microRNAs. In certain embodiments, the microRNA-associated protein exports microRNAs from the cell. In certain embodiments, the microRNA-associated protein is nucleolin. In certain embodiments, the microRNA-associated protein is nucleophosmin.

In certain embodiments, the microRNA is any natural microRNA. In certain embodiments, more than one microRNA is tested. In certain embodiments, a library of microRNAs is tested. In certain embodiments, synthetic microRNA is tested.

In certain embodiments, competition assays are conducted to determine whether a test compound is capable of competing with a single microRNA for a protein associated protein. In certain embodiments, a test compound is tested for its ability to compete with more than one different microRNA. Thus, assays may be performed to identify a selective competitive microRNA modulator, which competes with one or more microRNA to a greater extent than it competes with one or more other microRNA. In certain instances, a selective competitive microRNA modulator competes or displaces one microRNA, but fails to compete with another microRNA. This may be due to differing affinities or binding characteristics among different microRNAs for the microRNA-associated protein. Since such selective competitive microRNA modulators modulate one or more microRNA more than at least one other microRNA, they have specific uses. In certain instances, a selective competitive microRNA modulator is capable of modulating a single microRNA to a greater degree than it modulates any other microRNA.

In certain embodiments, assays are used to identify broad competitive microRNA modulators. In certain embodiments, broad competitive microRNA modulators are capable of competing with more than one microRNA. In certain embodiments, broad competitive microRNA modulators are capable of competing with at least half of the natural microRNAs. In certain embodiments, broad competitive microRNA modulators are capable of competing with essential all microRNAs. In certain embodiments, broad competitive microRNA modulators are capable of competing with all microRNAs. Such broad competitive microRNA modulators alter the "miR tone," or overall microRNA activity in a cell. Because microRNAs are involved in regulation of expression of many object proteins, broad competitive microRNA modulators are expected to have profound consequences in cells.

Certain microRNAs are known to regulate several object mRNAs and in some cases hundreds of object mRNAs. Inhibiting the activity of a single microRNA can lead to detectable changes in expression of many of such object mRNAs. Provided herein are methods for modulating multiple microRNA targets, wherein broad gene expression changes occur. In certain embodiments, one may detect competitive microRNA modulation indirectly by assessing changes in one or more object mRNA or protein or even further indirectly by measuring a consequence of the change in the amount of one or more object mRNAs.

For example, in certain instances, a compound capable of competing with miR133, 331, 339, 532, and/or 615 for Ago2 results in a decrease in the activity of those microRNAs. That decrease in microRNA activity de-represses (and thus, increases) expression of several transcripts, including the protease granzyme B, which in turn is responsible for, among other things, degrading α-tubulin. Thus, in certain embodiments, competition of a test compound may assessed by contacting a cell with the test compound and assessing any of: binding of the test compound to Ago2; decrease in binding of miR133, 331, 339, 532, and/or 615 to Ago2; increase in granzyme B expression, or decrease in α-tubulin level in the cell. Compounds identified by such methods are useful for increasing granzyme B and/or reducing α-tubulin in a cell. Since α-tubulin is important for many cellular functions, such compounds may be used in certain embodiments to reduce cell viability, for example in cancer treatment.

MicroRNAs are found to be associated with a variety of diseases. In certain embodiments, the microRNA is associated with a disease, and provided herein are methods for modulating the disease comprising administering a competitive microRNA modulator described herein to an individual having the disease. In certain embodiments, the methods comprise treating the disease. In certain embodiments, the methods comprise preventing the disease. In certain embodiments, the methods comprise delaying the onset of the disease.

D. CERTAIN COMPETITIVE MICRORNA MODULATORS

In certain embodiments, the present invention provides methods of predicting or assessing the ability of a test compound to modulate microRNA activity by competing with the microRNA for a microRNA-associated protein. Such methods may be performed using any molecule suspected of having the ability to compete (a test compound or test competitive microRNA modulator). In certain embodiments, the test compound may be a synthetic small molecule or a peptide. In certain embodiments, test compounds are oligomeric compounds, such as oligonucleotides. Such oligonucleotides may be single stranded or they may be double stranded. In certain embodiments, such oligonucleotides comprise one or more modifications. In certain embodiments, competitive microRNA modulators are double-stranded oligonucleotides comprising at least one modified nucleoside, wherein essentially each nucleoside is RNA or RNA-like.

Since the activity of competitive microRNA modulators derives from their ability to competitively bind to a microRNA-associated protein, and does not necessarily derive from hybridization to a target nucleic acid, competitive microRNA modulators that are oligonucleotides may have any nucleobase sequence. It is expected that different nucleobase sequences result in differing competitive activity. Accordingly, in certain embodiments, the nucleobase sequence of a competitive microRNA modulator is selected for its ability to compete for a microRNA-associated protein. In certain embodiments, a competitive microRNA modulator is also an antisense compound—that is, it has a nucleobase sequence that is complementary to a target nucleic acid. Such compounds may have duel activity of modulating a target nucleic acid through antisense and modulating one or more microRNA activity through competitive binding of a microRNA-associated protein. In certain embodiments, a competitive microRNA modulator that is also an antisense compound is single stranded. In certain embodiments, a competitive microRNA modulator that is also an antisense compound is double stranded. In certain embodiments, a competitive microRNA modulator that is also an antisense compound is an RNAi agent (uses the RISC mechanism). In certain embodiments, a competitive microRNA modulator that is also an antisense compound is an siRNA.

a. Oligomeric Compounds

In certain embodiments, competitive microRNA modulators are oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications. Such chemical modifications include modifications of one or more nucleoside (including modifications to the sugar moiety and/or the nucleobase) and/or modifications to one or more internucleoside linkage.

i. Certain Modified Nucleosides

In certain embodiments, provided herein are oligomeric compounds comprising or consisting of oligonuleotides comprising at least one modified nucleoside. Such modified nucleosides comprise a modified sugar moeity, a modified nucleobase, or both a modifed sugar moiety and a modified nucleobase.

1. Certain Modified Sugar Moieties

In certain embodiments, competitive microRNA modulators comprise oligomeric compounds comprising one or more modifed nucleosides comprising a modifed sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substitued sugar moieties. In certain embodiments, modified sugar moieties are sugar surrogates. Such sugar surogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$)) where each R$_m$ and R$_n$ is, independently, H, an amino protecting group or substituted or unsubstituted C$_1$-C$_{10}$ alkyl.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)$_3$-2', 4'-(CH$_2$)—O-2' (LNA); 4'-(CH$_2$)—S-2; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., *J. Org. Chem.*, 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) Ethylene(methoxy) (4'-(CH(CH$_2$OMe)-O-2') BNA (also referred to as constrained MOE or cMOE) as depicted below.

(A)
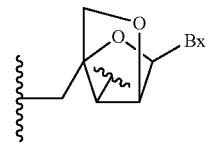

(B)
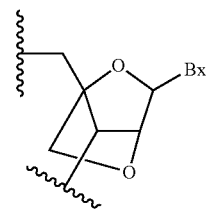

(C)
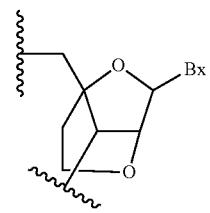

(D)
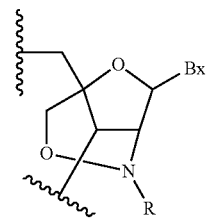

(E)
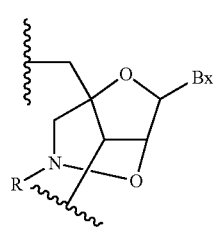

(F)
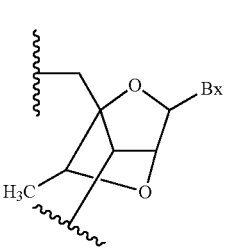

(G)
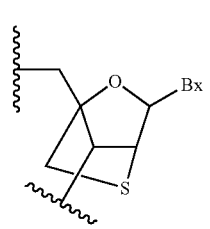

(H)
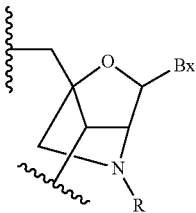

(I)
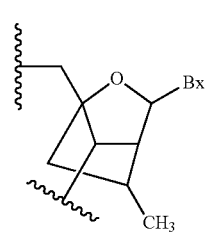

(J)
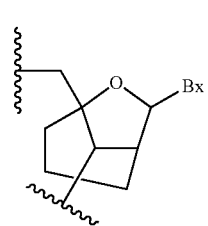

(K)
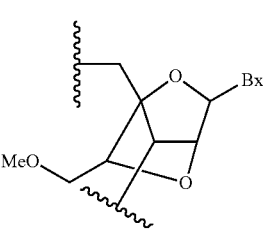

wherein Bx is a nucleobase moiety and R is, independently, H, a protecting group, or C$_1$-C$_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') bicyclic nucleosides have been incorporated into antisense oligonucleotides that showed antisense activity (Frieden et al., *Nucleic Acids Research,* 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surogates comprise a 4'-sulfur atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research,* 1997, 25(22), 4429-4443 and Albaek et al., *J. Org. Chem.,* 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA).

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry,* 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, the present invention provides oligonucleotides comprising modified nucleosides. Those modified nucleotides may include modified sugars, modified nucleobases, and/or modified linkages. The specific modifications are selected such that the resulting oligonucleotides possess desireable characteristics. In certain embodmiments, oligonucleotides comprise one or more RNA-like nucleosides. In certain embodiments, oligonucleotides comprise one or more DNA-like nucleotides.

2. Certain Modified Nucleobases

In certain embodiments, nucleosides of the present invention comprise one or more unmodified nucleobases. In certain embodiments, nucleosides of the present invention comprise one or more modifed nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering,* Kroschwitz, J. I., Ed., John Wiley & Sons, 1990, 858-859; those disclosed by Englisch et al., *Angewandte Chemie,* International Edition, 1991, 30, 613; and those disclosed by Sanghvi, Y. S., Chapter 15, *Antisense Research and Applications,* Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

ii. Certain Internucleoside Linkages

In certain embodiments, nucleosides may be linked together using any internucleoside linkage to form oligonucleotides. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(═O)—N(H)-5'), amide-4 (3'-CH$_2$—N(H)—C(═O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

b. Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

c. Certain Conjugate Groups

In certain embodiments, competitive microRNA modulators are oligomeric compounds that are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3'end of an oligomeric compound, but before one or more terminal group nucleosides. In certain embodiments, conjugate groups are placed within a terminal group. In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the motifs discussed above. Thus, for example, an oligomeric compound comprising an oligonucleotide having region of alternating nucleosides may comprise a terminal group.

h. Compositions and Methods for Formulating Pharmaceutical Compositions

Oligomeric compounds may be mixed with pharmaceutically acceptable active and/or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Oligomeric compounds, including siRNAs, can be utilized in pharmaceutical compositions by combining such oligomeric compounds with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in certain embodiments, employed in the methods described herein is a pharmaceutical composition comprising an siRNA compound and a pharmaceutically acceptable diluent. In certain embodiments, the pharmaceutically acceptable diluent is PBS.

Pharmaceutical compositions comprising oligomeric compounds encompass any pharmaceutically acceptable salts, esters, or salts of such esters. In certain embodiments, pharmaceutical compositions comprising oligomeric compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active oligomeric compound.

Lipid-based vectors have been used in nucleic acid therapies in a variety of methods. In one method, the nucleic acid is introduced into preformed liposomes or lipoplexes made of mixtures of cationic lipids and neutral lipids. In another method, DNA complexes with mono- or poly-cationic lipids are formed without the presence of a neutral lipid.

In certain methods, preparations are made that include a polyamine compound or a lipid moiety complexed with a nucleic acid. In certain embodiments, such preparations comprise one or more compounds each individually having a structure defined by formula (I) or a pharmaceutically acceptable salt thereof, formula (I)

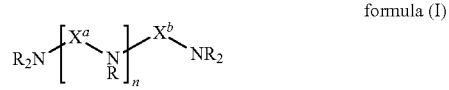

wherein each $X^a$ and $X^b$, for each occurrence, is independently $C_{1-6}$ alkylene; n is 0, 1, 2, 3, 4, or 5; each R is independently H, wherein at least n+2 of the R moieties in at least about 80% of the molecules of the compound of formula (I) in the preparation are not H; m is 1, 2, 3 or 4; Y is O, $NR^2$, or S; $R^1$ is alkyl, alkenyl, or alkynyl; each of which is optionally substituted with one or more substituents; and $R^2$ is H, alkyl, alkenyl, or alkynyl; each of which is optionally substituted each of which is optionally substituted with one or more substituents; provided that, if n=0, then at least n+3 of the R moieties are not H. Such preparations are described in PCT publication WO/2008/042973, which is herein incorporated by reference in its entirety.

Certain preparations, some of which are shown below, are described in Akinc et al., *Nature Biotechnology* 26, 561-569 (1 May 2008), which is herein incorporated by reference in its entirety.

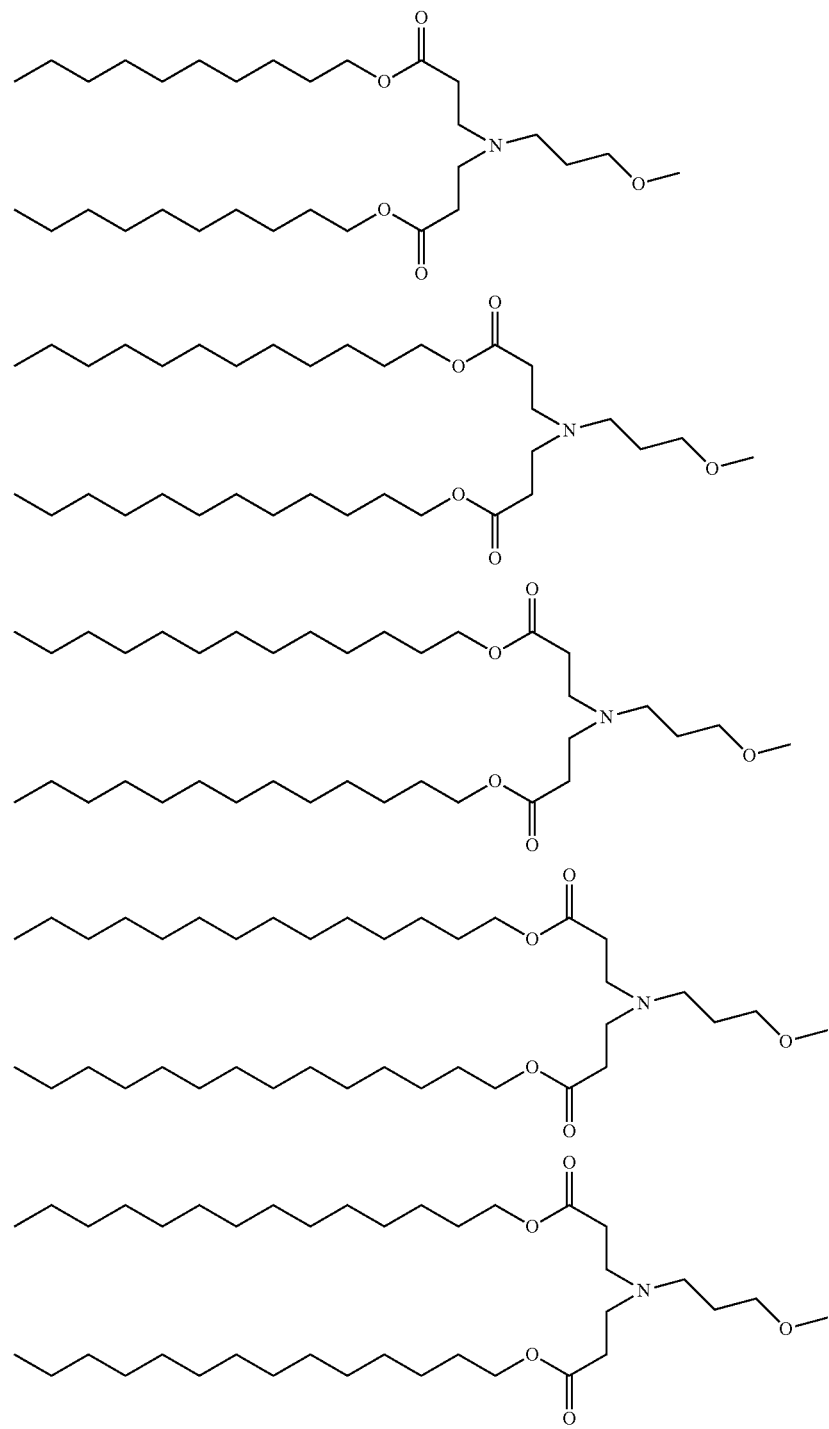

-continued
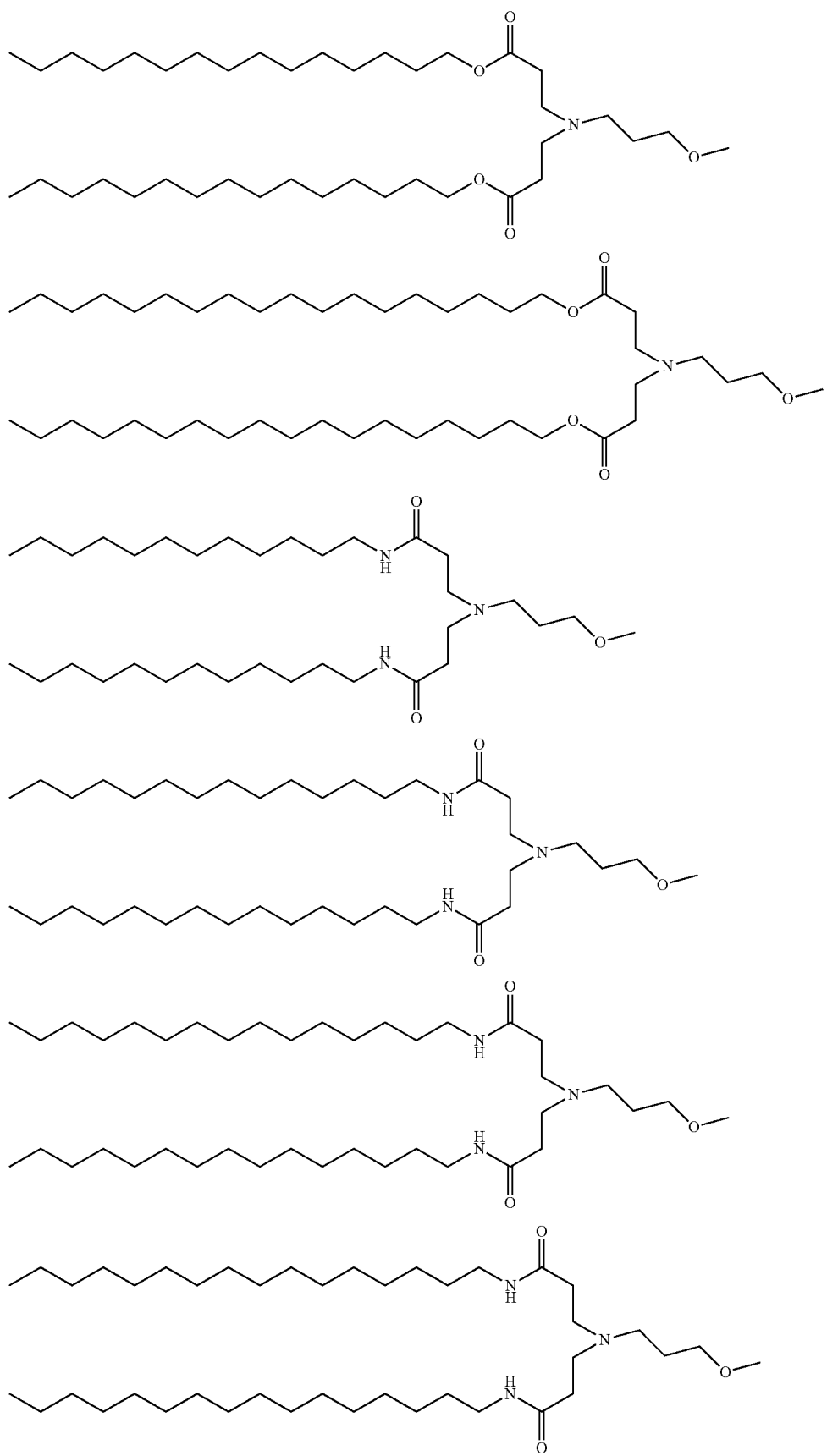

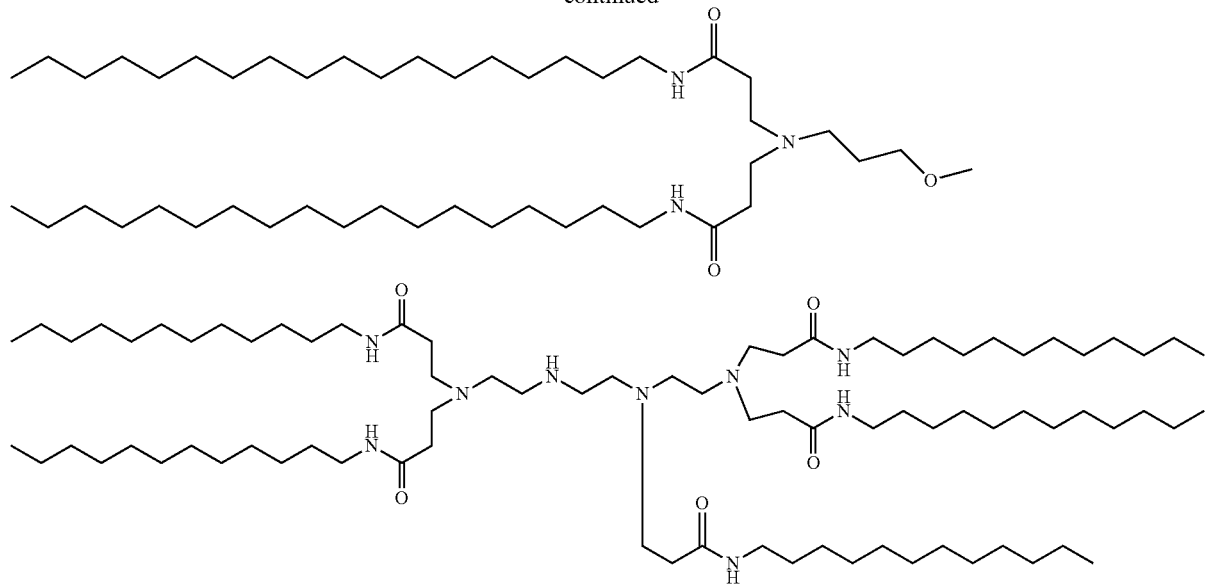

25

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif And, for example, where a particular high-affinity modification appears at a particular position, other high-affinity modifications at the same position are considered suitable, unless otherwise indicated.

Example 1

Materials and Methods

Materials

Antibodies, siRNAs, RNaseH-dependent oligonucleotides, qRT-PCR primers and probes, and oligonucleotide probes for northern hybridization are as follows.

Antibodies

Antibodies against RNase H1 and H2 that were raised in rabbit are gifts from Hong-jiang Wu. Antibodies for α-tubulin (T5168, 1:8000), β-tubulin (T5293, 1:6000), γ-tubulin (T6557, 1:6000) and β-actin (A5316, 1:6000) were purchased from Sigma. Antibodies against hnRNPA2/B1 (ab6102, 1:1000), nucleolin (ab13541, 1:1000), Ubiquitin (ab7780, 1:500), RHA (ab26271, 1:1000), GAPDH (ab8245, 1:1000), Ago2 (ab57113, 1:1000), Fen1 (ab17993, 1:1000), GZMM (ab55226, 1:1000) were from Abcam. RPL4 antibody (11302-1-AP, 1:1000) was from Proteintech. Rio2 (NBP1-30098, 1:1000) and MRTO4 (H00051154-D01, 1:1000) antibodies were from Novus. Secondary antibodies (1:2000) conjugated with HRP for mouse (172-1019) and rabbit (172-1011) were purchased from Bio-Rad. Anti-mouse secondary antibody conjugated with FITC (ab6785) and anti-rabbit secondary antibody conjugated with Texas Red (ab6719) were from Abcam.

Antisense Oligonucleotides(ASOs) Used for Northern Hybridization

The sequences of antisense oligonucleotides used for northern hybridization are presented in Table 1a. Each nucleoside throughout the oligonucleotide is ribonucleoside and all the internucleoside linkages are phosphodiester (P=O) linkages.

TABLE 1a

Antisense oligonucleotides (ASOs) used for northern hybridization

| ASO | Composition (5' to 3') | RNA | SEQ ID NO |
|---|---|---|---|
| XL137 | AACTATACAACCTACTACCTCA | Let-7a | 1 |
| XL138 | CGCCAATATTTACGTGCTGCTA | miR-16 | 2 |
| XL139 | CTACCTGCACTGTAAGCACTTTG | miR-17 | 3 |
| XL140 | TCAGTTTTGCATGGATTTGCACA | miR-19b | 4 |
| XL141 | TCAACATCAGTCTGATAAGCTA | miR-21 | 5 |
| XL142 | CTGTTCCTGCTGAACTGAGCCA | miR-24 | 6 |
| XL143 | GCGGAACTTAGCCACTGTGAA | miR-27a | 7 |
| XL144 | ACAGGCCGGGACAAGTGCAATA | miR-92 | 8 |
| XL011 | TTGCTCAGTAAGAATTTTCG | U16 snoRNA | 9 |
| XL018 | AATACCAGGTCGATGCGTGG | U2 snRNA | 10 | qRT-PCR Primer Probe Sets

The sequences for α-tubulin primer/probe set used in qRT-PCR are as follows. 5'-GTGAAACTGGTGCTG-GAAAAC (forward primer) (SEQ ID NO: 11); 5'-CAG-CATCCTCTTTCCCAGTG-3' (reverse primer) (SEQ ID NO: 12); and 5'-AAATGGCCCATACCGACAGCTCTT-3' (probe) (SEQ ID NO: 13).

The sequences for GZMB primer/probe set used in qRT-PCR are as follows. 5'-GGGATGGGTCTTTTCACAGG-3' (forward primer) (SEQ ID NO: 14) 5'-CGGTGGCTTCCT-GATACAAG-3' (reverse) (SEQ ID NO: 15); and 5'-CTGGGTCGGCTCCTGTTCTTTGA-3' (probe) (SEQ ID NO: 16).

The sequences for GZMM primer/probe set used in qRT-PCR are as follows. 5'-GCATGTGTAACAACAGC-CGCTTCT-3' (forward primer) (SEQ ID NO: 17); 5'-TT-GAAGATGTCAGTGCAGACCCTG-3' (reverse) (SEQ ID NO: 18); and 5'-TGTTGGCCGGAGTCCTGTCCTTCA-3' (probe) (SEQ ID NO: 19).

The sequences for MOV10 primer/probe set used in qRT-PCR are as follows. 5'-ATGGTGTGGATGTG-GAAGTC-3' (forward primer) (SEQ ID NO: 20); 5'-AGAGTGGGAAGAGGTGAGTG-3' (reverse) (SEQ ID NO: 21); and 5'-TTGAACCGCAAAGAGGTGCTGAC-3' (probe) (SEQ ID NO: 22).

The sequences for Fen1 primer/probe set used in qRT-PCR are as follows. 5'-GGGCCGCCTGGATGAT-3' (forward primer) (SEQ ID NO: 23); 5'-TGGCTCCTTGCGCT-TAGC-3' (reverse) (SEQ ID NO: 24); and 5'-TCTTCAAGGTGACCGGCTCACTCTCTTC-3' (probe) (SEQ ID NO: 25).

The sequences for RHA primer/probe set used in qRT-PCR are as follows. 5'-CCACTTACTGATACTCCT-GACAC-3' (forward primer) (SEQ ID NO: 26); 5'-CAG-GAACACCATAGCCAGAG-3' (reverse) (SEQ ID NO: 27); and 5'-TGCTTTGAGAGCCAGATGTGGAGG-3' (probe) (SEQ ID NO: 28).

The sequences for DHX30 primer/probe set used in qRT-PCR are as follows. 5'-AAAAGAGTTCCCACA-GCCC-3' (forward primer) (SEQ ID NO: 29); 5'-GGC-CATTTTATGTGCAGTGTG-3' (reverse) (SEQ ID NO: 30); and 5'-AGTGTGATTGGAAGAGCCCTCGG-3' (probe) (SEQ ID NO: 31).

The sequences for DHX36 primer/probe set used in qRT-PCR are as follows. 5'-GAAAGAGGAAAAGGATCT-GCTTG-3' (forward primer) (SEQ ID NO: 32); 5'-AC-CGATCTGGAGACGAATTTG-3' (reverse) (SEQ ID NO: 33); and 5'-TTACCACTGCCACAAGATTCTGCCC-3' (probe) (SEQ ID NO: 34).

The sequences for Rnase H1 primer/probe set used in qRT-PCR are as follows. 5'-CCTGTACTTACTGGTGTG-GAAAATAGC-3' (forward primer) (SEQ ID NO: 35); 5'-CCGTGTGAAAGACGCATCTG-3' (reverse) (SEQ ID NO: 36); and 5'-TGCAGGTAGGACCATTGCAGT-GATGG-3' (probe) (SEQ ID NO: 37).

The sequences for Rnase H2 primer/probe set used in qRT-PCR are as follows. 5'-TCCTCAATGAAGGGTC-CCAA-3' (forward primer) (SEQ ID NO: 38); 5'-GC-CGCGTTCCAGGAAATAT-3' (reverse) (SEQ ID NO: 39); and 5'-CCCGTCCCGTTCTTCCCACC-3' (probe) (SEQ ID NO: 40).

The sequences for PTEN primer/probe set used in qRT-PCR are as follows. 5'-AATGGCTAAGTGAAGAT-GACAATCAT-3' (forward primer) (SEQ ID NO: 41); 5'-TGCACATATCATTACACCAGTTCGT-3' (reverse) (SEQ ID NO: 42); and 5'-TTGCAGCAATTCACTG-TAAAGCTGGAAAGG-3' (probe) (SEQ ID NO: 43). Primer probe sets for PTEN siRNA (sense and antisense) were customized and purchased from Applied Biosystems, based on the siRNA sequence (sense, 5'-AAGUAAGGAC-CAGAGACAA-3' (SEQ ID NO: 44); antisense, 5'-UUGU-CUCUGGUCCUUACUU-3' (SEQ ID NO: 45)).

The sequences for OAS1 primer/probe set used in qRT-PCR are as follows. 5'-CCGCATGCAAATCAACCAT-3' (forward primer) (SEQ ID NO: 46); 5'-GCTACCTCG-GAAGCACCTTTC-3' (reverse) (SEQ ID NO: 47); and 5'-CCATTGACATCATCTGTGGGTTCCTGAA-3' (probe) (SEQ ID NO: 48).

The sequences for U16 primer/probe set used in qRT-PCR are as follows. 5'-CTTGCAATGATGTCGTAATTTGC-3' (forward primer) (SEQ ID NO: 49); 5'-TCGTCAACCT-TCTGTACCAGCTT-3' (reverse) (SEQ ID NO: 50); and 5'-TTACTCTGTTCTCAGCGACAGTTGCCTGC-3' (probe) (SEQ ID NO: 51).

The sequences for Nucleolin primer/probe set used in qRT-PCR are as follows. 5'-GCTTGGCTTCTTCTG-GACTCA-3' (forward primer) (SEQ ID NO: 52); 5'-TCGC-GAGCTTCACCATGA-3' (reverse) (SEQ ID NO: 53); and 5'-CGCCACTTGTCCGCTTCACACTCC-3' (probe) (SEQ ID NO: 54).

TaqMan miRNA Assays Used to Detect miRNAs qRT-PCR primer probe sets for detecting miRNAs were purchased from Applied Biosystems and assay IDs are as follows. miR-16 (000391); miR-17 (002308); miR-21 (000397); miR-24 (000402); miR-27a (000408); miR-378 (002243); miR-422a (002297); miR-133a (002246); miR-331-3p (000545); miR-339-5p (002257); miR-532-3p (002355) and miR-615-5p (002353).

Cell Culture and Transfection

HeLa, HEK293, mouse embryonic fibroblast (MEF) cells, Ago2 knock cells, and MHT cells (a gift from Eric Koller)

were cultured in DMEM supplemented with 10% FBS, 0.1 µg/ml streptomycin, and 100 units/ml penicillin. Transfection of siRNAs was performed in DMEM medium supplemented with 10% FBS, using 5 µg/ml lipofectamin RNAiMAX or 4 µg/ml Lipofectamin 2000 or Oligofectamin according to the manufacture's procedure. Unless otherwise stated, starting cell confluency was at approximately 50-70%.

Western Analysis

Equal amount of proteins (8-20 µg) were separated in 4-12% SDS PAGE, transferred to membrane. Blocking and detection of proteins was performed as described in Liang et al., *Nucleic Acids Research*, 2010, 1-17.

Northern Hybridization and qRT-PCR

Northern hybridization and qRT-PCR using TaqMan primer probe sets were performed as described in Liang et al., *Nucleic Acids Research*, 2010, 1-17. For miRNA detection, total RNA was isolated from cells using miRNeasy kit (Qiagen) and miRNA was either detected by northern hybridization, or by qRT-PCR using TaqMan miRNA assay (Applied Biosystems) according to manufacturer's protocol.

Immunoprecipitation

Whole cell extracts prepared in Buffer A [25 mM Tris.Cl pH 8.0]; 5 mM $MgCl_2$; 150 mM KCl; 10% glycerol; 0.5 mM PMSF; 5 mM β-mercaptoethanol; and one tablet of Protease Inhibitor Cocktail/50 ml (Roche) were incubated at 4° C. for 4 hours with Protein A beads (Roche) pre-coated with antibody against Ago2 (ab57113), α-tubulin (T5168), or RIO2 (NBP1-30098). After six washes with wash buffer (50 mM Tris.Cl, pH7.5; 150 mM NaCl; 5 mM EDTA; 0.1% NP-40; 0.05% SDS), the co-selected proteins were directly separated by loading the boiled beads into SDS-PAGE. The co-immunoprecipitated RNAs were prepared directly from the beads using Tri-Reagent and subjected to reverse transcription-qRT-PCR analysis.

Translation Shut-Off

HeLa cells were transfected with or without 8 nM Fen1 siRNA for 48 hrs. Medium was then replaced with pre-warmed DMEM medium supplemented with 10% FBS and 15 µg/ml cycloheximide. Cells were collected at different times using trypsine and the protein levels were detected by western analysis.

Example 2

Effect of siRNAs on Target Protein Degredation

To examine the effect of siRNAs on protein degradation (e.g. α-tubulin, hnRNP A2, γ-tubulin, nucleolin, RPL4, MTRO4, Ubiquitin), eight siRNAs were selected and evaluated.

siRNAs

The synthesis and purification of ISIS 341401 was performed using similar methods as described in Baker et al., *J. Biol. Chem*, 272, 11994-12000. Unless otherwise stated, the pre-designed siRNAs were purchased from commercial sources and the composition of the sense strand is presented in Table 1. The internucleoside linkages throughout each siRNA are phosphodiester (P=O) linkages. Nucleosides with capitalized letters indicate ribonucleosides (RNAs). Nucleosides with small letters "tt" indicate 2'-β-deoxyribonucleosides overhang.

Compositions for the following siRNAs, sc88358, s14450, s48358 and s20656 can be obtained from the manufacturers.

Cell Culture, Transfection, and Analysis

HeLa cells were maintained in DMEM supplemented with 10% FBS, 0.1 µg/ml streptomycin, and 100 units/ml penicillin. Transfection of siRNAs from Table 1 at 5 nM concentration was performed in DMEM medium supplemented with 10% FBS, using 5 µg/ml lipofectamin RNAiMAX according to the manufacture's procedure. "UTC" indicates untreated control. "Mov10" indicates cells transfected with sc-88358 siRNA targeting Mov10. "RHA" indicates cells transfected with s4019 siRNA targeting RHA/DHX9. "DHX30" indicates cells transfected with s22643 siRNA targeting DHX30. "DHX36" indicates cells transfected with s46822 siRNA targeting DHX36. "TSNAX" indicates cells transfected with s14450 siRNA targeting TSNAX. "H1" indicates cells transfected with s48358 siRNA targeting Rnase H1. "H2" indicates cells transfected with s20656 siRNA targeting Rnase H2A. "PTEN" indicates cells transfected with ISIS 341401 siRNA targeting PTEN. Starting cell confluency was approximately at 50%. After 48 hrs, western analysis for various proteins (i.e. α-tubulin, hnRNP A2, γ-tubulin, nucleolin, RPL4, MTRO4 and Ubiquitin) was performed using the procedures described in Example 1. Equal amount of proteins (~10 µg) were separated by 4-12% gradient SDS-PAGE, transferred to membranes and different proteins were sequentially detected. Quantification of α-tubulin protein levels was measured using ImageJ and normalized to hnRNP A2. The results are presented in FIGS. 1 and 2.

Figure 2:
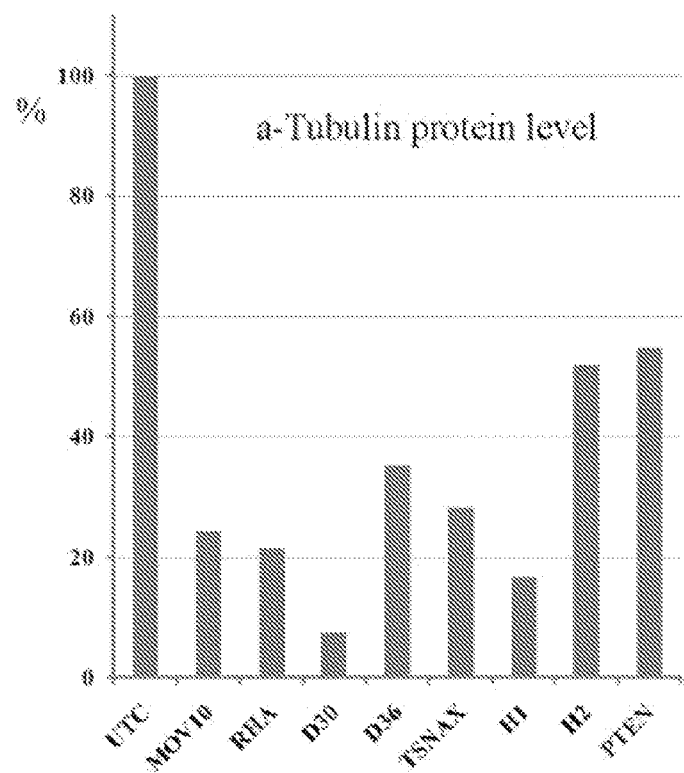
FIG. 2 shows quantification of α-tubulin protein levels normalized to hnRNP A2 protein levels in the western blot depicted in FIG. 1.

As illustrated, α-tubulin protein levels were significantly reduced in cells transfected with siRNAs targeting various targets comparing to untreated control (UTC). Further, similar reduction was also observed for nucleolin protein in siRNA-treated cells as illustrated in FIG. 1. No significant reduction was detected for other target proteins examined, including hnRNP A2, RPL4, γ-tubulin, and MTRO4.

TABLE 1 siRNAs targeting various targets

| siRNA catalog no. | Target | Company | Composition (only sense strand is shown) | SEQ ID NO. |
|---|---|---|---|---|
| sc-88358 | MOV10 | Santa Cruz Biotechnology | — | |
| s4019 | RHA (DHX9) | Applied Biosystems | 5'-GAGUGUAACAUCGUAGUAAtt-3' | 55 |
| s22643 | DHX30 | Applied Biosystems | 5'-GGACCAUAGAUGUUACCGAtt-3' | 56 |
| s46822 | DHX36 | Applied Biosystems | 5'-CAGUGUUAGUCAUAUCGUAtt-3' | 57 |

TABLE 1-continued siRNAs targeting various targets

| siRNA catalog no. | Target | Company | Composition (only sense strand is shown) | SEQ ID NO. |
|---|---|---|---|---|
| s14450 | TSNAX | Ambion | — | |
| s48358 | Rnase H1 | Ambion | — | |
| s20656 | Rnase H2A | Ambion | — | |
| ISIS 341401 | PTEN | ISIS Pharm. | 5'-AAGUAAGGACCAGAGACAA-3' | 58 |

Example 3

Dose-Dependent Effect of RHA siRNAs on α-Tubulin Reduction

To further examine if the reduction of α-tubulin is directly related to siRNA, a dose-dependent study was performed. One siRNA from Table 1 (s4019) was selected and evaluated.

Cell Culture, Transfection, and Analysis

HeLa cells were cultured in DMEM supplemented with 10% FBS, 0.1 μg/ml streptomycin, and 100 units/ml penicillin. Cells were transfected with siRNA (s4019) targeting RHA at 0, 0.5, 1, 2, 4 and 8 nM concentrations for 36 hours using similar transfection methods as described in Example 1. γ-tubulin was used as a loading control with cell confluency at approximately 50%. Western analysis was used as described in Example 1 to evaluate the dose-dependent effect of siRNA on α-tubulin protein levels. The results are presented in FIG. 3.

Figure 3:
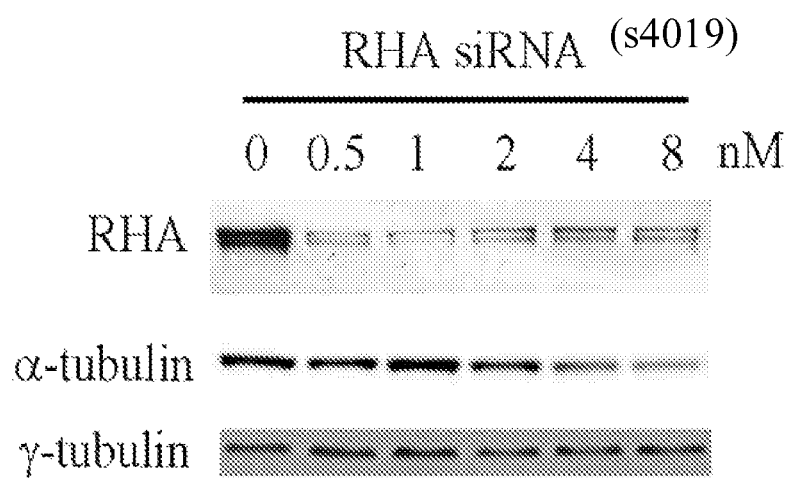
FIG. 3 shows a western blot illustrating RHA and tubulin protein levels following various doses of RHA siRNA treatment in HeLa cells.

As illustrated in FIG. 3, reduction of α-tubulin was affected in a dose-dependent manner. For example, 45-60% α-tubulin reduction was observed at high siRNA concentrations (4-8 nM) while the targeted protein RHA was significantly reduced at a lower concentration (0.5 nM). That the γ-tubulin level was not significantly affected shows that in certain embodiments, not all microtubule related proteins are equally affected by siRNA transfection.

Example 4

Dose-Dependent Effect of siRNAs on Tubulin Reduction

To confirm the dose-dependent effect of siRNAs on tubulin reduction, a different siRNA (HSS176903) was selected and evaluated.

siRNA

Unless otherwise stated, the pre-designed siRNA (HSS176903) was purchased from Invitrogen and the sequence for the sense strand is 5'-CAGGAACAGUUU-GUGGAUCUGUGCA-3' (SEQ ID NO: 59). Each nucleoside throughout the oligonucleotide is ribonucleosides and all the internucleoside linkages are phosphodiester (P═O) linkages.

Cell Culture, Transfection, and Analysis

HeLa cells were cultured in DMEM supplemented with 10% FBS. Cells with approximately 50% confluency were transfected with HSS176903 siRNA targeting Fen1 at 0, 1, 2, 4 and 8 nM concentrations for 36 hours using similar transfection methods as described in Example 1. γ-tubulin was used as a loading control. Western analysis was used as described in Example 1 to evaluate the dose-dependent effect of siRNA on target protein levels (i.e. α-tubulin, nucleolin or β-actin). Quantification of protein levels was measured using ImageJ and normalized to γ-tubulin. The results are presented in FIGS. 4 and 5.

Figure 4:
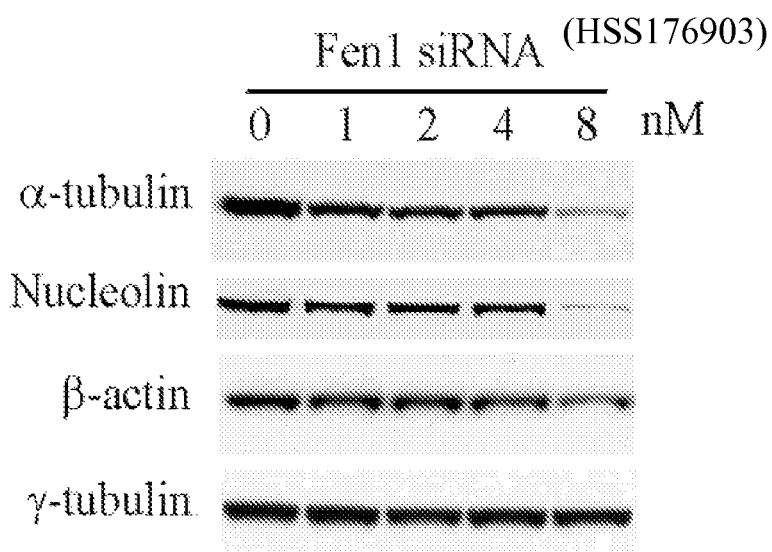
FIG. 4 shows a western blot illustrating tubulin, nucleolin, and actin protein levels following various doses of Fen1 siRNA treatment in HeLa cells.
Figure 5:
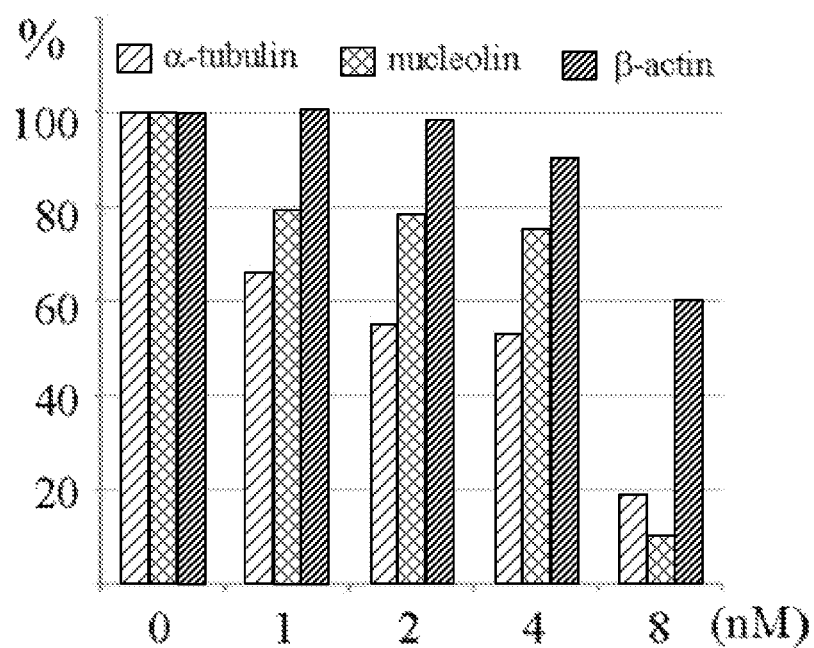
FIG. 5 shows quantification of α-tubulin, β-tubulin, and nucleolin protein levels normalized to γ-tubulin protein levels in the western blot depicted in FIG. 4.

As illustrated in FIGS. 4 and 5, reduction of α-tubulin was affected in a dose-dependent manner. Further, reduction of nucleolin and β-actin protein levels at 85% and 40% respectively, could be detected at high concentration of siRNA (8 nM). Taken together, these results show that in certain embodiments, other proteins can also be affected by siRNA transfection.

Example 5

Additive Effect of siRNAs on α-Tubulin Protein Reduction

To examine the effect of siRNAs on α-tubulin reduction when used a single siRNA alone or in combination with other siRNAs, two siRNAs from Examples 2 and 4 (HSS176903 and ISIS 341401) were selected and evaluated.

Cell Culture, Transfection, and Analysisμ

HeLa cells were cultured in DMEM supplemented with 10% FBS, 0.1 μg/ml streptomycin, and 100 units/ml penicillin. Cells were transfected for 48 hours with siRNAs (HSS176903 or ISIS 341401 alone or in combination) at various concentrations as presented in Table 2 using similar transfection methods as described in Example 1. Western analysis was used to evaluate the dose-dependent effect of siRNA on α-tubulin protein level. GAPDH was used as a loading control. Quantification of α-tubulin protein level was measured using ImageJ and normalized to GAPDH. The results are presented in FIGS. 6 and 7.

Figure 6:
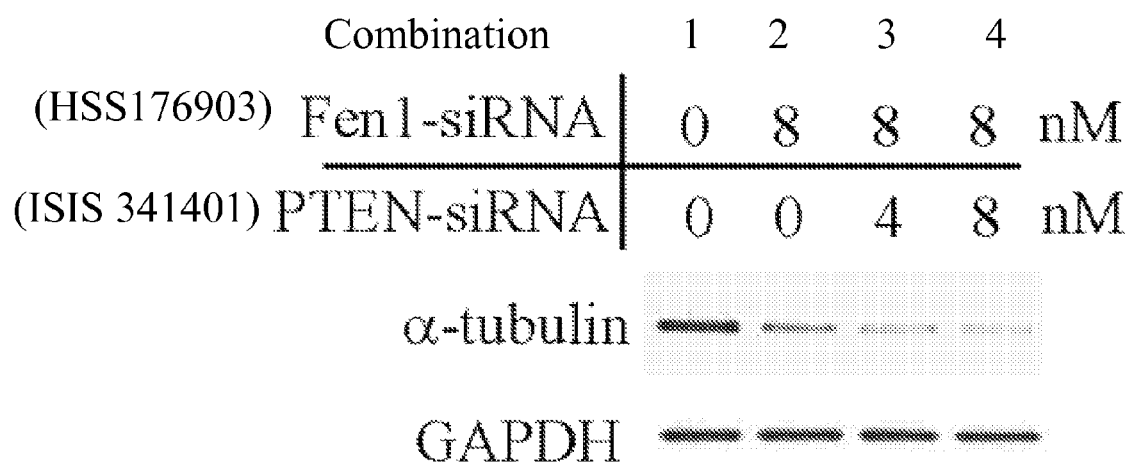
FIG. 6 shows a western blot illustrating α-tubulin and GAPDH protein levels following individual and combination treatment of HeLa cells with Fen1 siRNA and/or PTEN siRNA.
Figure 7:
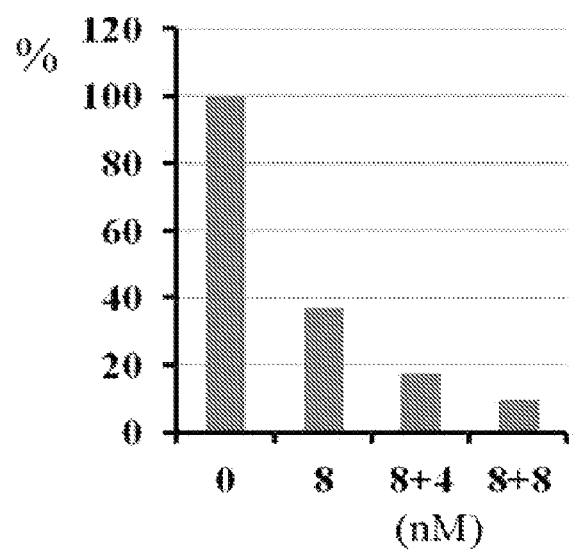
FIG. 7 shows quantification of α-tubulin protein levels normalized to GAPDH protein levels in the western blot depicted in FIG. 6.

As illustrated in FIGS. 6 and 7, significant reduction of α-tubulin was observed in a dose-dependent manner when used alone or in combination with other siRNAs.

TABLE 2 siRNAs used in the evaluation of siRNAs on α-tubulin level

| | | siRNA catalog no. | |
|---|---|---|---|
| | | HSS176903 | ISIS 341401 |
| | SEQ ID NO. | 59 | 58 |
| Concentration (nM) | Combination 1 | 0 | 0 |
| | Combination 2 | 8 | 0 |
| | Combination 3 | 8 | 4 |
| | Combination 4 | 8 | 8 |

Example 6

Effect of siRNAs on α-Tubulin Protein Level in Mouse MHT Cells

To examine the effect of siRNAs on α-tubulin reduction in mouse MHT cells targeting various targets (Fen1-03, Fen1-27, MOv10, hVPS28 and mVPS28), several siRNAs were selected and evaluated.

siRNAs

Unless otherwise stated, the pre-designed siRNAs were purchased from commercial sources and the composition of the sense strand is presented in Table 1. The internucleoside linkages throughout each siRNA are phosphodiester (P=O) linkages. Nucleosides with capitalized letters indicate ribonucleosides (RNAs). Nucleosides with small letters "tt" indicate 2'-β-deoxyribonucleosides overhang.

Composition for sc-88358 siRNA can be obtained from the manufacturer.

Cell Culture, Transfection, and Analysis

Mouse MHT cells were cultured in DMEM supplemented with 10% FBS, 0.1 µg/ml streptomycin, and 100 units/ml penicillin. Cells were transfected for 24 hours with 8 nM concentration of siRNAs in Table 3 targeting different human and mouse genes using similar transfection methods as described in Example 1. "UTC" indicates untreated control. "Fen1-03" indicates cells transfected with HSS176903 siRNA targeting Fen1-03. "Fen1-27" indicates cells transfected with HSS103627 siRNA targeting Fen1-27. "Mov10" indicates cells transfected with sc-88358 siRNA targeting Mov10. "hVPS28" indicates cells transfected with hVPS28 siRNA targeting human VPS28. "mVPS28" indicates cells transfected with mVPS28 siRNa targeting mouse VPS28. Coomassie blue staining of a duplicate gel was used as loading control. Western analysis was used as described in Example 1 to evaluate the effect of siRNA on α-tubulin. Quantification of α-tubulin protein level was measured using ImageJ. The results are presented in FIGS. 8 and 9.

Figure 8:
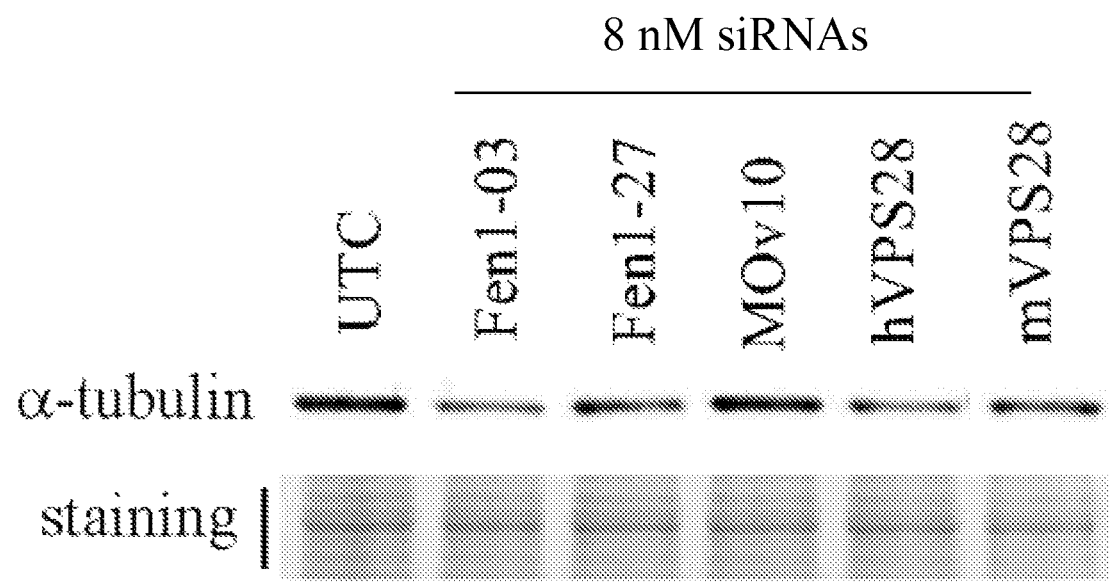
FIG. 8 shows a western blot illustrating α-tubulin protein levels following treatment of MHT cells with various siRNAs. A Coomassie blue stained gel is also shown as a loading control.
Figure 9:
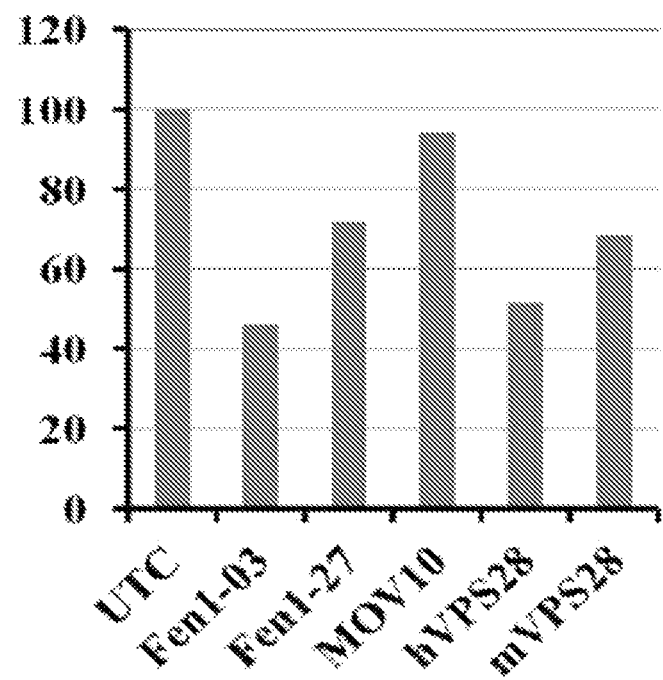
FIG. 9 shows quantification of α-tubulin protein levels relative to the untreated control in the western blot depicted in FIG. 8.

As illustrated in FIGS. 8 and 9, transfection of siRNAs can cause α-tubulin reduction as compared to untreated control (UTC) in all targets tested.

Example 7

Ago2 Effect on siRNA-Induced α-Tubulin Reduction

Since siRNAs associate with Ago2 to form RISC complexes, siRNA-induced α-tubulin reduction may thus depend on Ago2. To examine this hypothesis, two siRNAs from Table 2 (ISIS 341401 and HSS176903) were selected and evaluated.

Cell Culture, Transfection, and Analysis

Ago2 knockout (−/−Ago2) and mouse embryonic fibroblast (MEF) cells were transfected at 60% start confluency with siRNAs at 15 nM concentration for 36 hours using the transfection method as described in Example 1. "Fen1-si" indicates cells tranfected with HSS176903 siRNA targeting Fen1. "PTEN-si" indicates cells transfected with ISIS 341401 siRNA targeting PTEN. "UTC" indicates untreated control. Western analysis was used as described in Example 1 to evaluate the effect of siRNA on α-tubulin levels. Quantification of α-tubulin protein was measured using ImageJ and normalized to γ-tubulin. The results are presented in FIG. 10.

Figure 10:
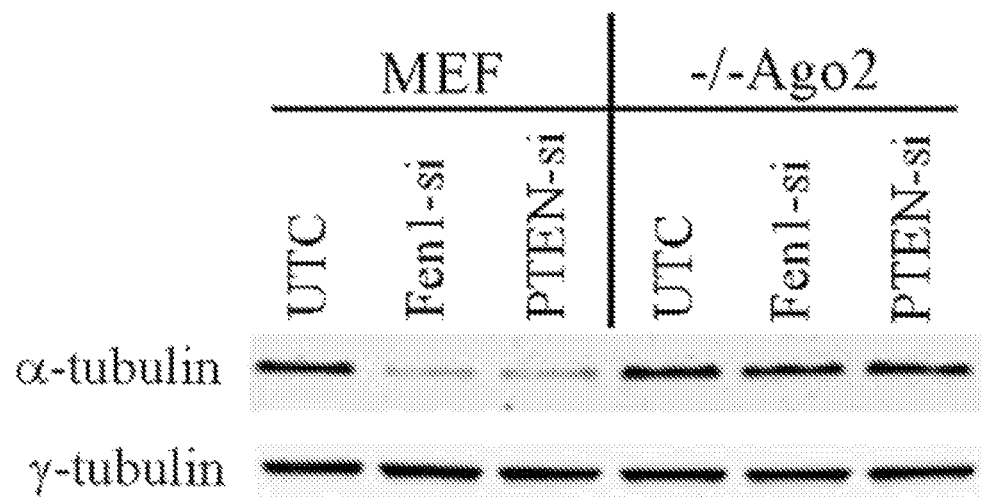
FIG. 10 shows a western blot illustrating α-tubulin and γ-tubulin protein levels following siRNA treatment of MEF and Ago2 knock-out cells.

As illustrated in FIG. 10, transfection of two different siRNAs into Ago2 knockout mouse cells had no obvious effect on α-tubulin level as compared to untreated control (UTC). In contrast, 80% reduction was detected in MEF cells treated with the same siRNAs. These results indicate that siRNA-induced α-tubulin reduction is Ago2-dependent.

Example 8

Effect of siRNAs or Ago2 on α-Tubulin Protein

To further investigate if siRNAs or Ago2 directly interact with tubulin protein since it has been shown that some microtubule-targeting reagents can lead to rapid degradation of tubulin protein by directly interacting with tubulin protein or microtubule (Harris et al., *Biochem. Biophys. Res. Comm.*, 2009, 388, 354-349; or Huff et al., *Cancer Res*, 2010, 70, 5870-5879). One siRNA from Table 1 (ISIS 341401) was selected and evaluated.

Cell Culture, Transfection, and Analysis

Cell lysate prepared from HeLa cells was transfected with ISIS 341401 siRNA at 5 nM concentration for 4 hours, and immunoprecipitation was performed using antibodies against Ago2, α-tubulin, or Rio2, as described in Example 1. Co-precipitated siRNA was analyzed by qRT-PCR. As a positive control, qRT-PCR was performed on RNA from 10% input material used for immunoprecipitation. The results are presented in FIG. 11, in which the error bars represent standard deviation of three parallel experiments and "(−)AB" means the immunoprecipitation procedure was performed without antibody. Co-precipitated proteins were analyzed by western analysis for the presence of α- or β-tubulin proteins and the results are presented in FIG. 12.

TABLE 3 siRNAs targeting various targets

| siRNA catalog no. | Target | Company | Composition (only sense strand is shown) | SEQ ID NO. |
|---|---|---|---|---|
| HSS176903 | Fen1-03 | Invitrogen | 5'-CAGGAACAGUUUGUGGAUCUGUGCA-3' | 59 |
| HSS103627 | Fen1-27 | Invitrogen | 5'-CAUCAAGCCCGUGUAUGUCUUUGAU-3' | 60 |
| sc-88358 | MOv10 | Santa Cruz Biotechnology | — | |
| hVPS28 | Human VPS28 | Applied Biosystems | 5'-GAAGUGAAGUUGUACAAGAtt-3' | 61 |
| mVPS28 | Mouse VPS28 | Applied Biosystems | 5'-GAAGTAAAGCTCTACAAGAtt-3' | 62 |

Figure 11:
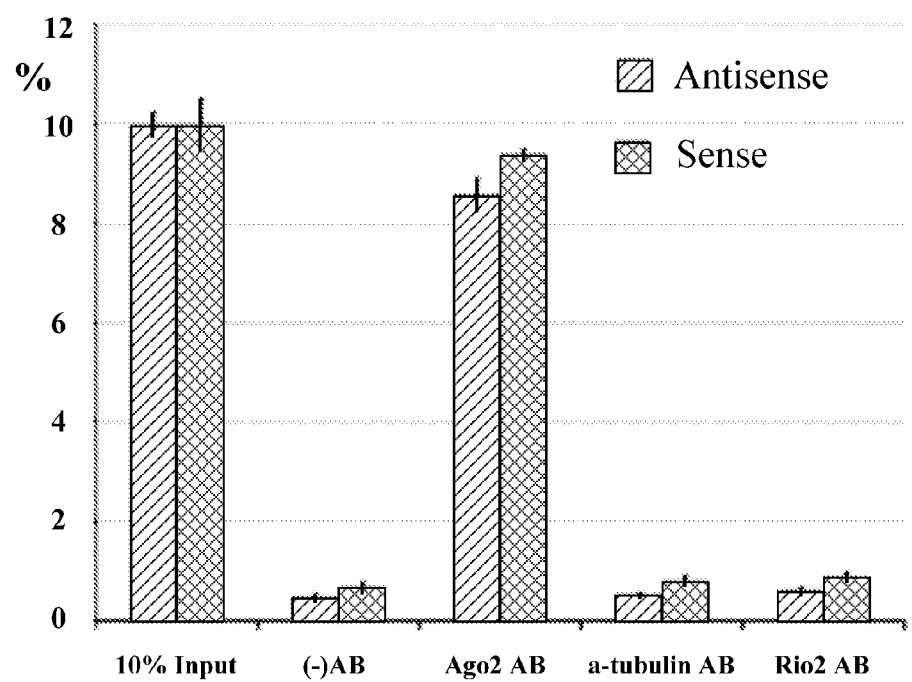
FIG. 11 shows RT-PCR results for siRNA Isis 341401 following treatment of HeLa cells with siRNA Isis 341401 in the HeLa cell lysate input and following immunoprecipitation of HeLa cell lysates with various antibodies.
Figure 12:
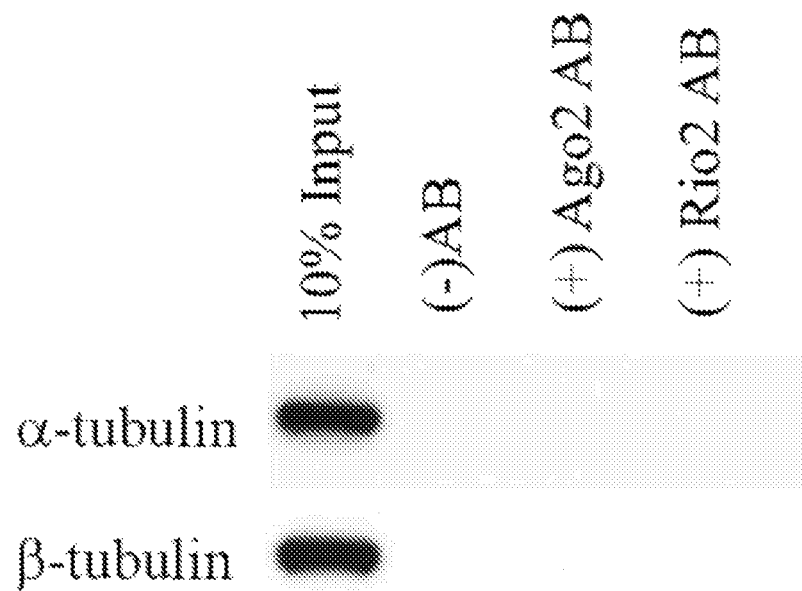
FIG. 12 shows a western blot illustrating the protein levels of α-tubulin and β-tubulin in the HeLa cell lysate input and the immunoprecipitation elutes referred to in FIG. 11.

As illustrated in FIG. 11, neither sense nor antisense siRNA was significantly co-precipitated with α-tubulin protein. Ago2 antibodies were used as a positive control, and siRNA was significantly co-precipitated with Ago2 (FIG. 11). In addition, neither α- nor β-tubulin protein was co-immunoprecipitated with Ago2 (FIG. 12), demonstrating that in certain embodiments, tubulin reduction is not induced by direct interaction of siRNAs and/or Ago2 protein with α-tubulin protein.

Example 9

Effect of siRNA Transfection on Endogenous miRNAs

Since Ago2 protein is shared by both siRNAs and endogenous miRNAs, transfection of siRNA may thus compete with miRNAs for Ago2 protein, leading to disturbed miRNA expression or function, which in turn can cause tubulin reduction through mis-regulation of other genes. It has been shown that transfection of siRNA can affect global gene expression (Tagami et al., *Pharm. Res.*, 2008, 25, 2497-2504), most likely by perturbing gene regulation by miRNAs (Khan et al., *Nature Biotech.*, 2009, 27, 549-555).

Thus, to examine if transfection of siRNAs can cause reduction of miRNA levels due to competition for Ago2, the levels of three selected miRNAs (miR-21, miR-17, and miR-24) were evaluated.

siRNAs

The synthesis and purification of ISIS 341401 was performed using similar methods as described in Baker et al., *J. Biol. Chem*, 272, 11994-12000. Unless otherwise stated, the pre-designed siRNAs were purchased from commercial sources and the composition of the sense strand is presented in Table 4. Each nucleoside throughout the oligonucleotide is ribonucleosides. The internucleoside linkages throughout are phosphodiester (P=O) linkages.

Compositions for siRNAs, sc-88358 and s14431 can be obtained from the manufacturers.

Cell Culture, Transfection and Method

Mouse MEF cells were transfected at 70% confluency with siRNAs in Table 4 at 10 nM concentration using the transfection method as described in Example 1. "No-si or UTC" indicates non-transfected or untreated control. "MOv10-s or Mov10" indicates cells transfected with sc-88358 siRNA targeting Mov10. "PTEN-si or PTEN" indicates cells transfected with ISIS 341401 siRNA targeting PTEN. "TSN-si or TSN" indicates cells transfected with s14431 siRNA targeting TSN. Northern analysis of miRNAs in mouse MEF cells was performed after 24 hours post transfection. Total RNA (~8 µg/lane) was separated in a 10% polyacrylamide, 7 M urea gel, and transferred to membrane. Different miRNAs were detected by northern hybridization using 5' end-labeled probes, as described in Example 1. U16 snoRNA was used as a loading control. Quantification of endogenous miRNA levels was determined using ImageJ and normalized to U16. The blot is shown in FIG. 13, and the quantification is shown in FIG. 14.

Figure 13:
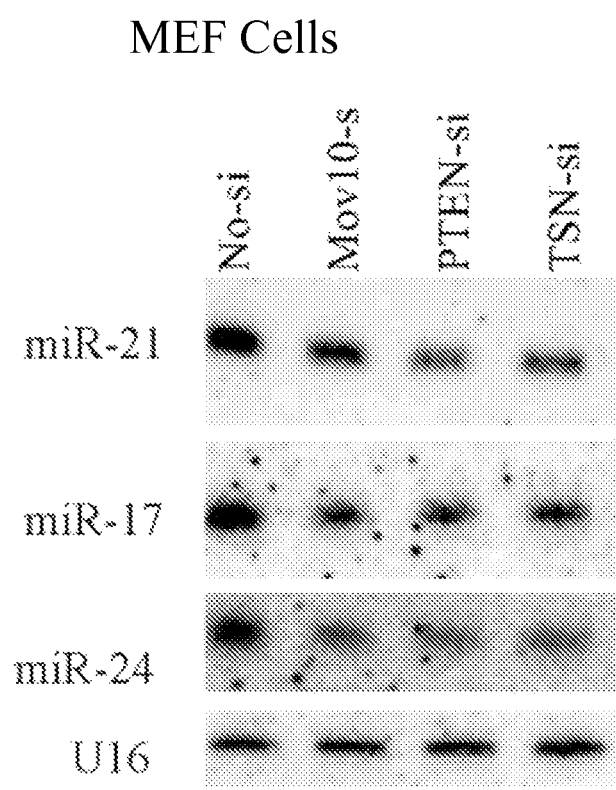
FIG. 13 shows a northern blot illustrating miRNA and U16 snoRNA levels following treatment of MEF cells with various siRNAs.
Figure 14:
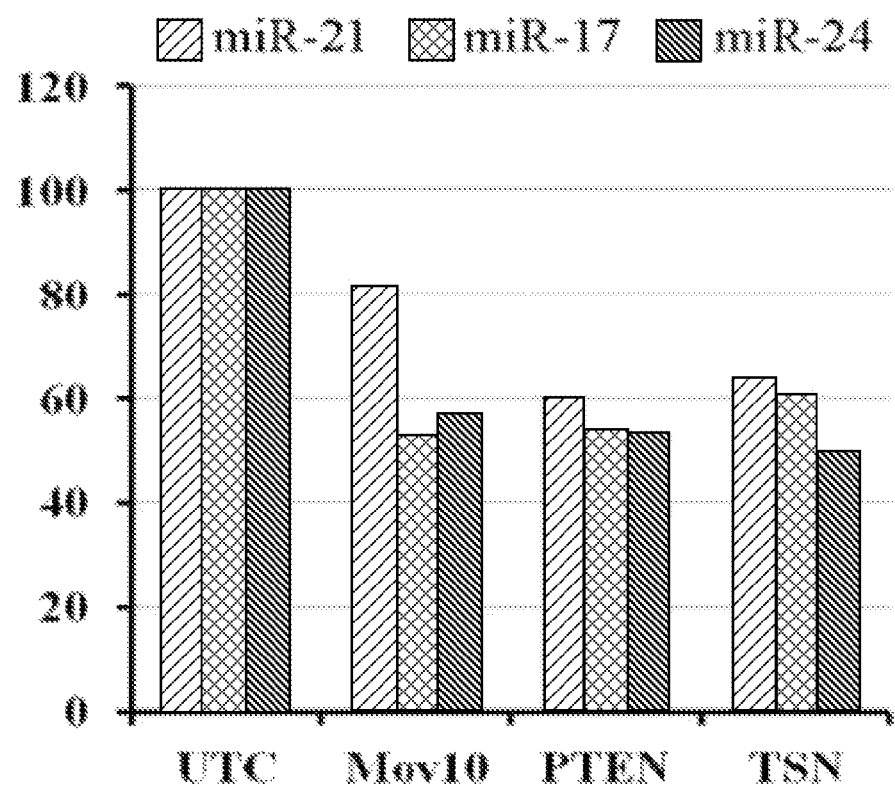
FIG. 14 shows quantification of miRNA levels normalized to U16 snoRNA in the northern blot depicted in FIG. 13.

As illustrated in FIGS. 13 and 14, the levels of three tested miRNAs (miR-21, miR-17, and miR-24) were reduced by approximately 20-50% in MEF cells transfected with different siRNAs as compared to non-transfected control.

TABLE 4

| siRNAs targeting various targets | | | | |
|---|---|---|---|---|
| siRNA cat. no. | Target | Company | Composition (only sense strand is shown) | SEQ ID NO. |
| sc-88358 | MOv10 | Santa Cruz Biotechnology | — | |
| ISIS 341401 | PTEN | ISIS Pharm. | 5'-AAGUAAGGACCAGAGACAA-3' | 58 |
| s14431 | TSN | Ambion | — | |

Example 10

Effect of siRNA Transfection on Endogenous miRNAs in HEK293 Cells

To further investigate the effect of siRNAs on endogenous miRNA-21, two siRNAs from Table 4 (ISIS 341401 and s14431) were selected and evaluated.

Cell Culture, Transfection and Analysis

HEK293 cells were transfected with PTEN or TSN siRNAs at 10 nM concentration for 48 hrs using transfection method as described in Example 1. "UTC" indicates untreated control. "PTEN" indicates cells transfected with ISIS 341401 siRNA targeting PTEN. "TSN" indicates cells transfected with s14431 siRNA targeting TSN. miRNA-21 was detected by northern hybridization. U2 snRNA was used as a loading control. Quantification of miR-21 level was measured using ImageJ and normalized to U2 using the analysis method as described in Example 1. The blot is shown in FIG. 15, and the quantification is shown in FIG. 16.

Figure 15:
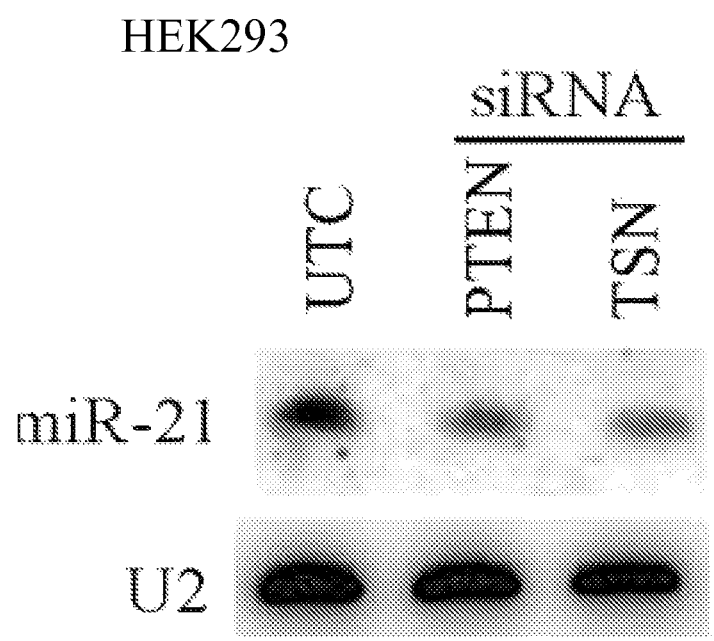
FIG. 15 shows a northern blot illustrating miR-21 and U2 snRNA levels following treatment of HEK293 cells with siRNA.
Figure 16:
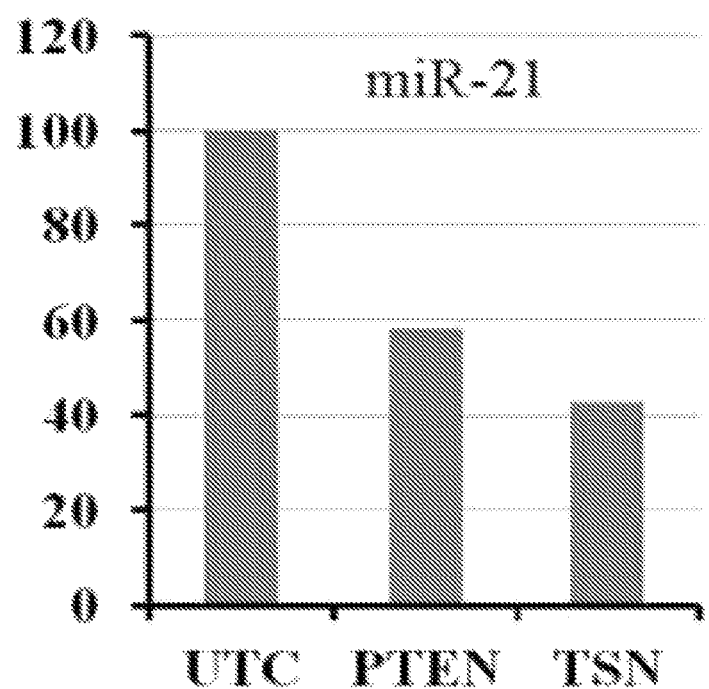
FIG. 16 shows quantification of miR-21 levels normalized to U2 snRNA levels in the northern blot depicted in FIG. 15.

As illustrated in FIGS. 15 and 16, reduction of miR-21 was observed in siRNA-transfected HEK293 cells.

Example 11

Dose-Dependent Effect of PTEN siRNAs on Endogeneous miRNA Levels

To examine the dose-dependent effect of siRNAs on endogenous miRNA levels, ISIS 341401 siRNA from Table 4 was selected and evaluated.

Cell Culture, Transfection, and Analysis

HeLa cells were cultured in DMEM supplemented with 10% FBS, 0.1 µg/ml streptomycin, and 100 units/ml penicillin. Cells were transfected with ISIS 341401 targeting PTEN at 0, 1, 5, 10, 20 and 30 concentrations for 36 hours using similar transfection methods as described in Example 1. miRNA levels were detected by Northern analysis as described in Example 1. U16 snoRNA was used as loading control. Quantification of miRNA levels was measured using ImageJ and normalized to U16. The blot is shown in FIG. 17, and the quantification is shown in FIG. 18.

Figure 17:
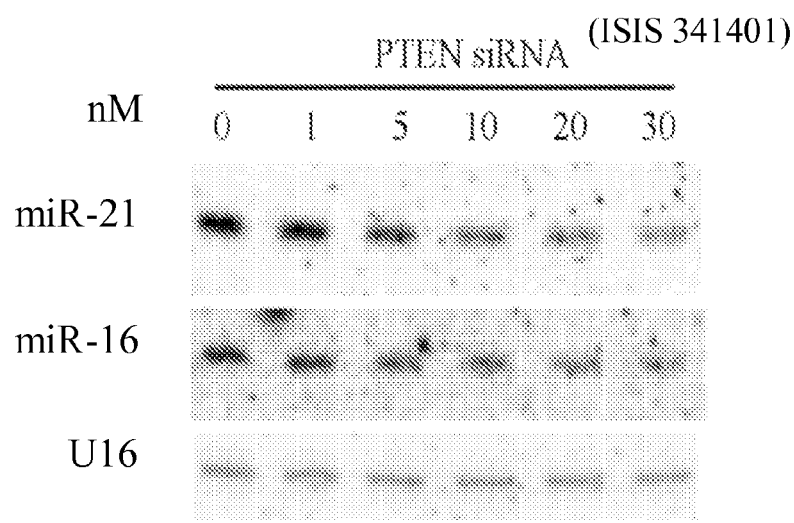
FIG. 17 shows a northern blot illustrating miRNA and U16 snoRNA levels following various doses of PTEN siRNA treatment in HeLa cells.
Figure 18:
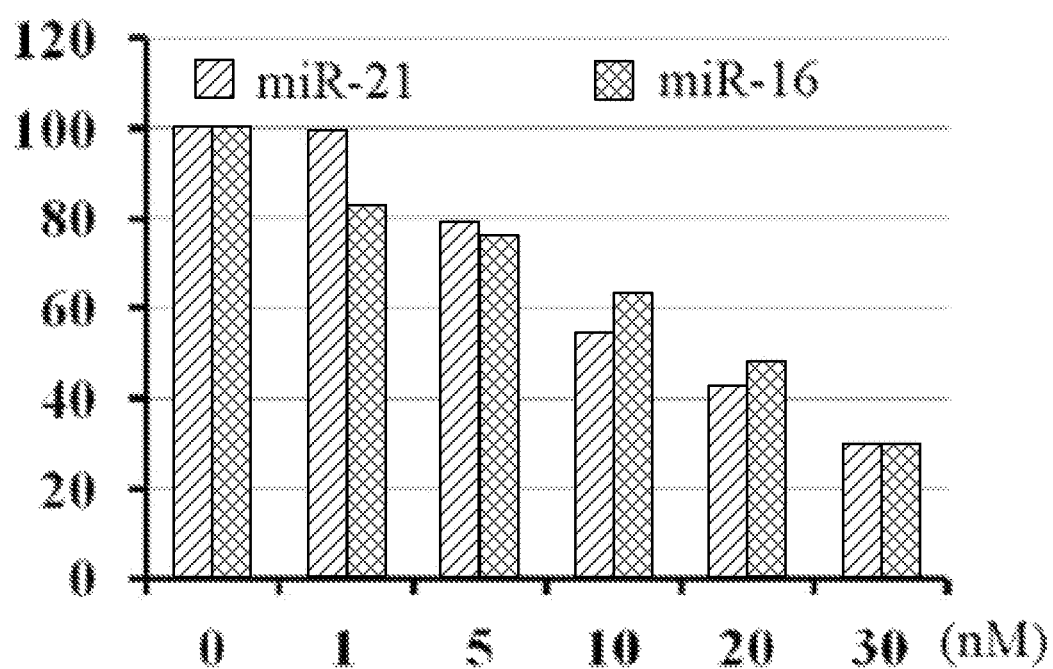
FIG. 18 shows quantification of miR-21 and miR-16 levels normalized to U16 snoRNA levels in the northern blot depicted in FIG. 17.

As illustrated in FIGS. 17 and 18, a dose-dependent reduction of miRNAs was observed with increasing siRNA concentrations, showing that in certain embodiments, siRNAs compete with miRNAs in a dose dependent manner.

Example 12

Dose-Dependent Effect of TSN siRNAs on Endogeneous miRNA Levels

To examine the dose-dependent effect of siRNAs on endogeneous miRNA levels, siRNA (s14431) targeting TSN from Table 4 was selected and evaluated.
Cell Culture, Transfection, and Analysis
HeLa cells were cultured in DMEM supplemented with 10% FBS, 0.1 µg/ml streptomycin, and 100 units/ml penicillin. Cells were transfected with siRNA (s14431) targeting TSN at 0, 1.5, 4.5, and 13.5 concentrations for 48 hours using similar transfection methods as described in Example 1. miRNA levels were detected by northern analysis as described in Example 1. U16 snoRNA was used as loading control. Quantification of miRNA levels was measured using ImageJ and normalized to U16. The blot is shown in FIG. 19, and the quantification is shown in FIG. 20.

Figure 19:
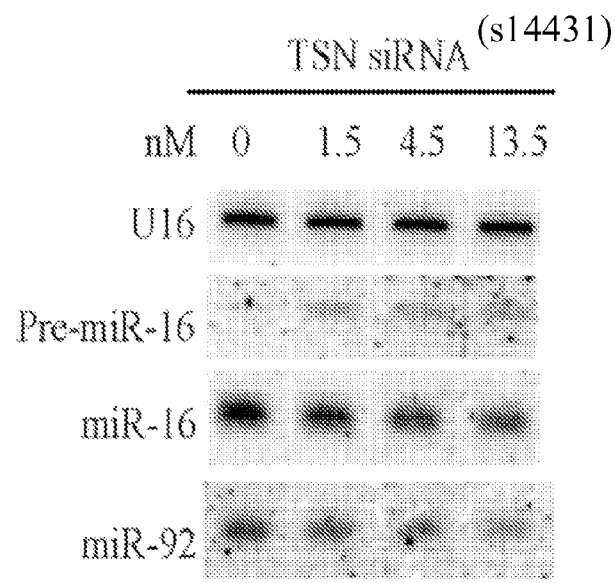
FIG. 19 shows a northern blot illustrating U16 snoRNA, pre-miR-16, miR-16, and miR-92 levels following various doses of TSN siRNA treatment in HeLa cells.
Figure 20:
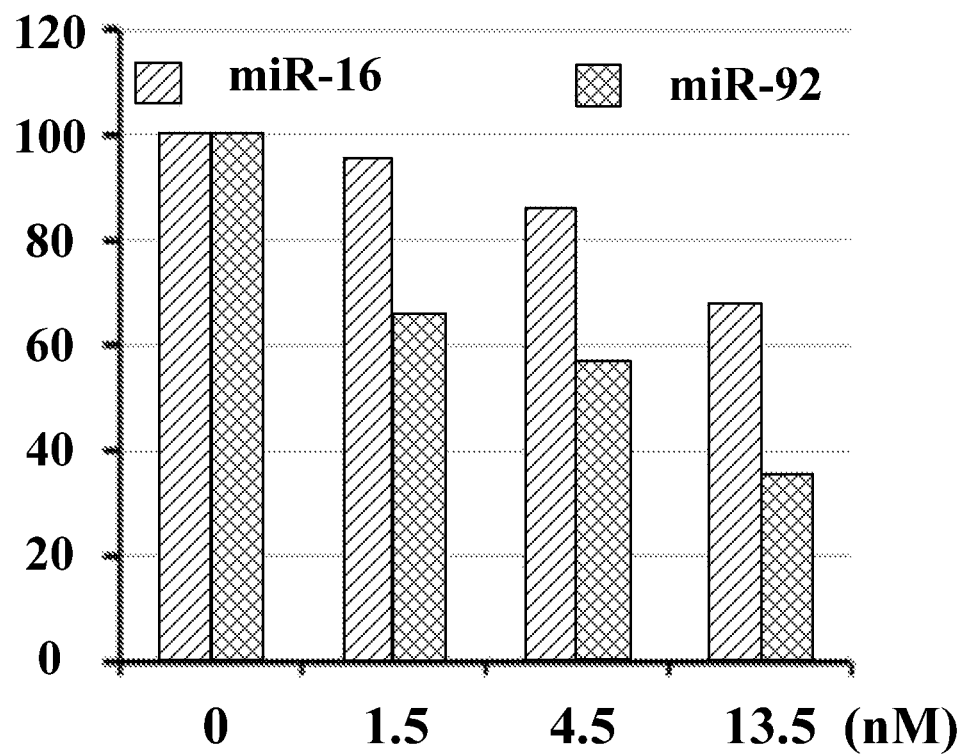
FIG. 20 shows quantification of miR-16 and miR-92 levels normalized to U17 snoRNA levels in the northern blot depicted in FIG. 19.

As illustrated in FIGS. 19 and 20, transfection of siRNA targeting TSN reduced the level of mature miR-16, yet the pre-miRNA level increased. This result demonstratess that in certain embodiments, transfection of siRNA can also disturb the miRNA biogenesis pathway.

Taken together, results from Examples 9-12 show that in certain embodiments, transfection of siRNAs can reduce the levels of many, if not all, miRNAs. Global reduction of miRNAs may thus cause mis-regulation of many genes, which in turn, can lead to tubulin reduction.

Example 13

Timecourse of miRNA Reduction Following siRNA Transfection

Figure 21:
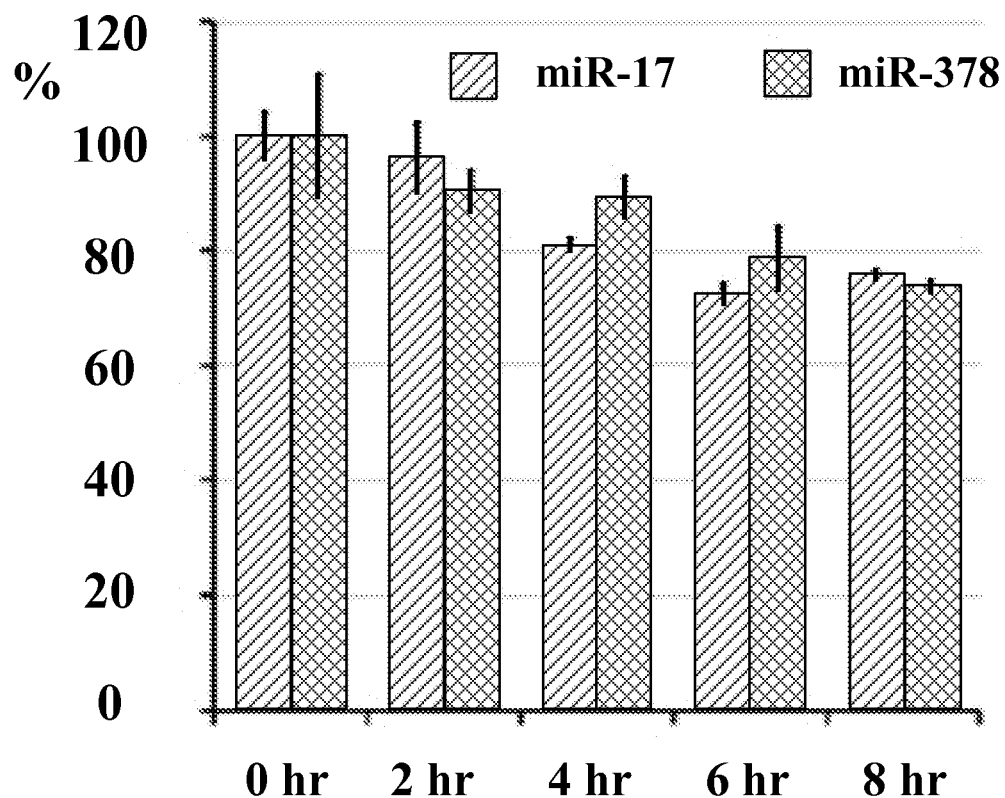
FIG. 21 shows miR-17 and miR-378 levels at various time points following treatment of HeLa cells with PTEN siRNA relative to miR-17 and miR-378 levels in untreated control HeLa cells.

If disrupted miRNA regulation is the cause of tubulin reduction, miRNA levels should be affected shortly after siRNA transfection since tubulin protein is quickly degraded following siRNA transfection (data not shown). Thus, the kinetics of the siRNA effect on miRNA levels (miR-17 and miR378) was determined siRNA (ISIS 341401) from Table 1 was selected and evaluated.
Cell Culture, Transfection and Analysis
HeLa cells were transfected with 8 nM PTEN siRNA (ISIS 341401) at various time points and the total RNA was prepared using miRNeasy kit. Endogenous miRNA levels were determined by qRT-PCR using TaqMan miRNA assay. The methods used to conduct the studies are described in Example 1, and the results are presented in FIG. 21.

Consistent with rapid degradation of tubulin protein, the levels of some miRNAs, such as miR-17 and miR-378, were gradually reduced after siRNA transfection, even at early time points (2-4 hrs). This is consistent with the data shown that targeted mRNAs could be significantly reduced 2 hrs after siRNA transfection (Vickers et al., *Nucleic Acids Research*, 2007, 35, 6598-6610). These results suggest that siRNAs compete with miRNAs, most likely for binding of Ago2 protein, leading to reduction of miRNAs that otherwise are protected by Ago2.

Example 14

Effect of siRNAs on Ago2-Bound miRNA Levels

To determine the effect of siRNA on Ago-2 bound miRNA levels (miR-17 and miR378), ISIS 341401 siRNA from Table 1 was selected and evaluated.
Cell Culture, Transfection and Analysis
HeLa cells were transfected with 8 nM concentration of PTEN siRNA (ISIS 341401) at various time points. miRNAs associated with Ago2 were isolated by immunoprecipitation from siRNA-treated cells, and co-immunoprecipitated miR-NAs were analyzed by qRT-PCR using the methods described in Example 1. Fen1 antibody was used as a negative control in the immunoprecipitation. The results are presented in FIG. 22.

Figure 23:
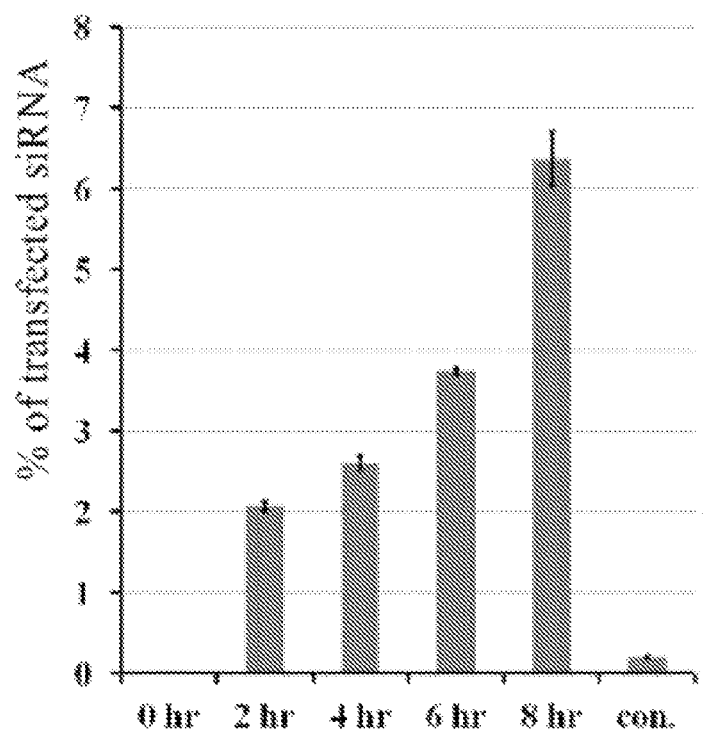
FIG. 23 shows levels of PTEN siRNA co-immunoprecipitated with an Ago2 antibody at various time points following treatment of HeLa cells with the PTEN siRNA.

Further, the same immunoprecipitated samples were analyzed for the level of co-precipitated PTEN siRNA (ISIS 341401) using qRT-PCR. The results are presented in FIG. 23, in which the error bars represent standard deviation from three parallel experiments.

In addition, aliquots of whole cell extract used as the input for the immunoprecipitation were analyzed by western blot to determine the levels of Ago2. γ-tubulin was used as a loading control. A non-specific product detected by Ago2 antibody is marked with an asterisk (*). The results are presented in FIG. 24.

Figure 22:
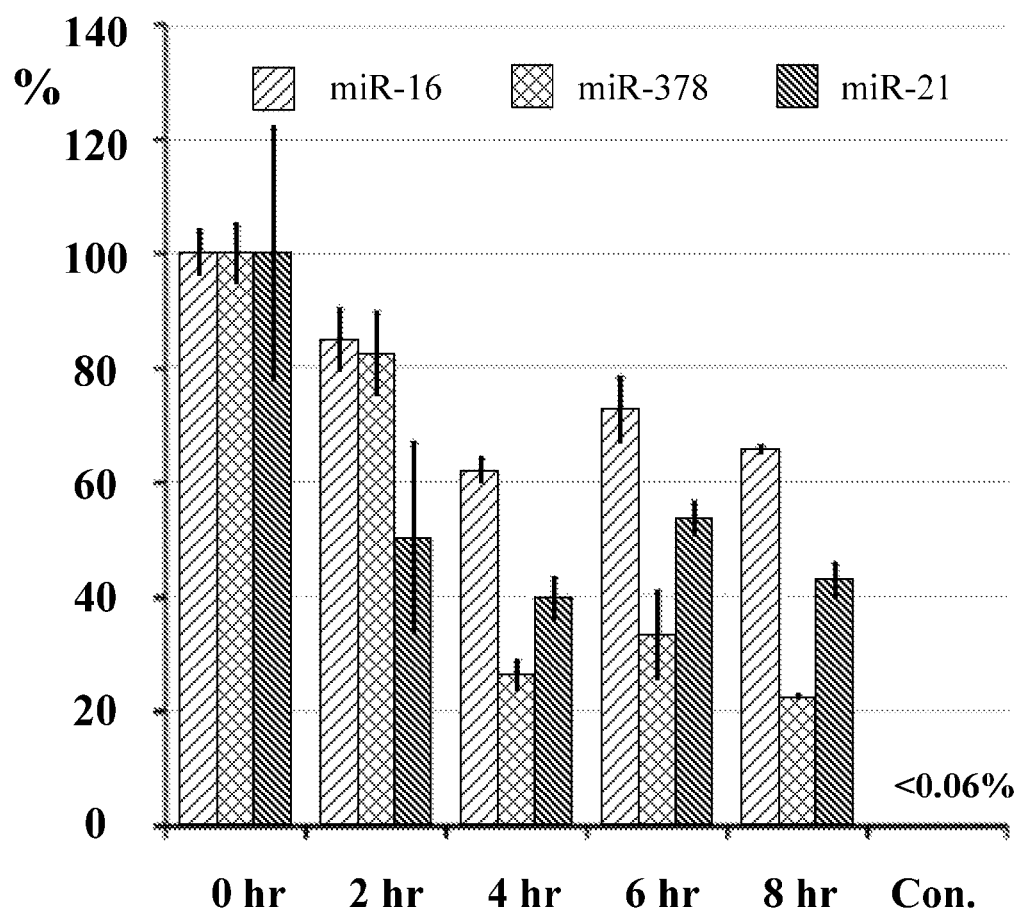
FIG. 22 shows levels of miRNA co-immunoprecipitated with an Ago2 antibody at various time points following treatment of HeLa cells with PTEN siRNA relative to levels of miRNA co-immunoprecipitated with an Ago2 antibody in untreated control HeLa cells.

As illustrated in FIG. 22, the levels of Ago2-bound miRNAs significantly reduced after siRNA transfection, as determined using RNA-immunoprecipitation with an Ago2 antibody. Significantly reduced level of Ago2-bound miR-378 was also observed, although the cellular level of this miRNA did not transiently increase upon siRNA transfection, suggesting that a portion of miR-378 lost association with Ago2.

Further, reduction of Ago2-bound miRNAs is accompanied by an increase in the levels of Ago2-bound siRNAs over time (FIG. 23), providing evidence that siRNAs compete with miRNAs for Ago2, leading to eventual reduction of miRNAs.

Figure 24:
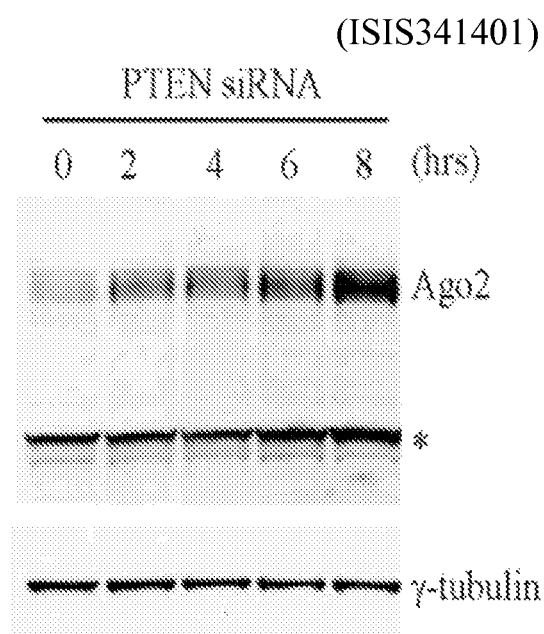
FIG. 24 shows a western blot illustrating Ago2 and γ-tubulin protein levels at various time points following treatment of HeLa cells with PTEN siRNA.

Consistently, reduction of Ago2-bound miRNAs is not due to unexpected reduction of Ago2 protein upon siRNA transfection, since the Ago2 level was actually up-regulated shortly after siRNA transfection (FIG. 24).

Taken together, these results suggest that transfection of siRNA can quickly compete and interfere with miRNA pathway, leading to rapid reduction of Ago2-bound miR-NAs.

Example 15

Depiction of miRNAs Potentially Targeting GZMB 3' UTR Region

Figure 25:
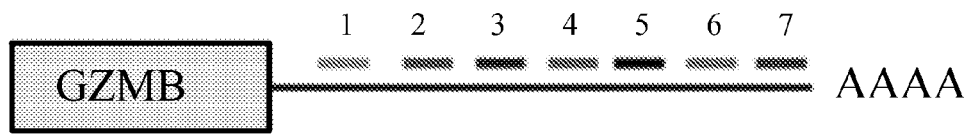
FIG. 25 shows a schematic depiction of the relative positions that miRNAs may potentially target the GZMB 3' UTR.

Schematic depiction of miRNAs potentially targeting GZMB 3' UTR region is illustrated in FIG. 25. The relative positions of miRNAs are indicated with colored bars, and names are shown with the corresponding colors. The gray box indicates the coding region of the mRNA.

Since rapid degradation of tubulin via siRNA transfection may also be mediated by proteases, like the case of small-molecule triggered tubulin degradation (Harris et al., *Biochem. Biophys. Res. Commun.*, 2009, 388, 345-349. Two proteases, Granzyme B (GZMB) and Granzyme M (GZMM), have been shown to be required for tubulin degradation (Bovenschen et al., *J. Immunol.*, 2008, 180, 8184-8191, and Goping et al., *J. Cell Sci.*, 2006, 119, 858-865). Thus, it is possible that siRNA induced α-tubulin reduction can be mediated by mis-regulation of these two proteases due to reduced level of miRNAs.

As depicted, the 3' UTR of GZMB can be potentially targeted by nine miRNAs, as predicted using a web-based server TargetScan (http://www.targetscan.org/). Two miRNAs (mir-378 and mir-422a) were selected, tested and evaluated as illustrated in the following example (Example 16).

Example 16 miRNA Levels in siRNA-Treated HeLa Cells

HeLa cells were transfected for 24 hours with H1 or Fen1 siRNAs selected from Examples 2 and 4 (s48358 or HSS176903) using the transfection methods as described in Example 1. "H1 siRNA" indicates cells transfected with s48358 targeting Rnase H1. "Fen1 siRNA" indicates cells transfected with HSS176903 targeting Fen1. Levels of miR-378 and miR-422a were detected using qRT-PCR as described in Example 1. The results are presented in FIG. 26.

Figure 26:
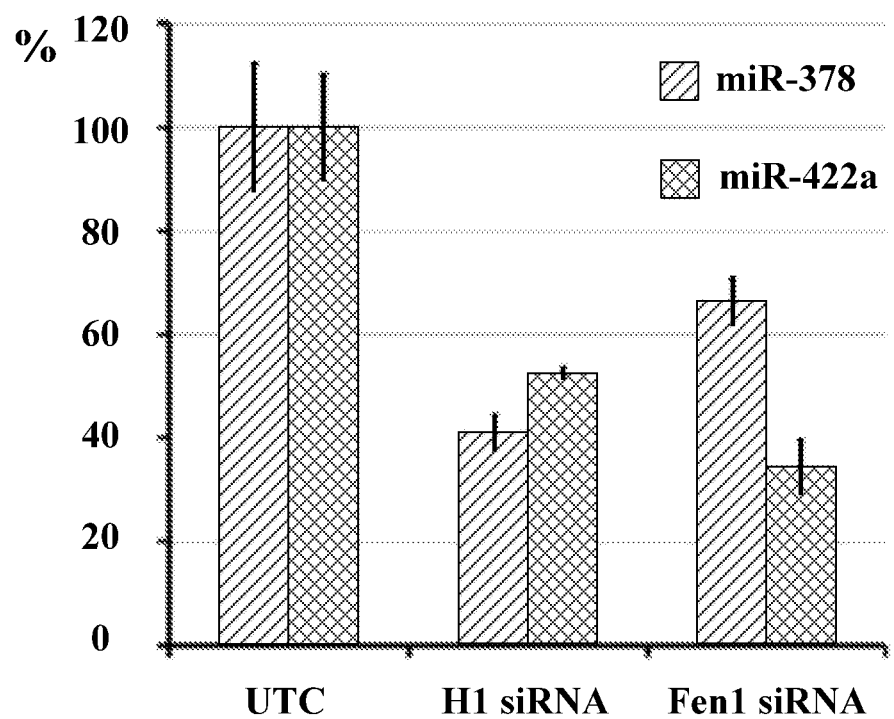
FIG. 26 shows miR-378 and miR-422a levels following treatment of HeLa cells with siRNA relative to miR-378 and miR-422a levels in untreated control HeLa cells.

As illustrated in FIG. 26, two tested miRNAs (miR-378 and miR-422a) were significantly reduced by transfection of siRNAs.

Example 17

Effect of siRNA on GZMB mRNA Level

To examine the effect of siRNA on GZMB expression, HeLa cells were transfected at 8 nM concentration for 36 hours with Fen1 siRNA (HSS176903) from Example 4 using the transfection methods as described in Example 1. Level of GZMB mRNA was determined by qRT-PCR as described in Example 1. The results are presented in FIG. 27.

Figure 27:
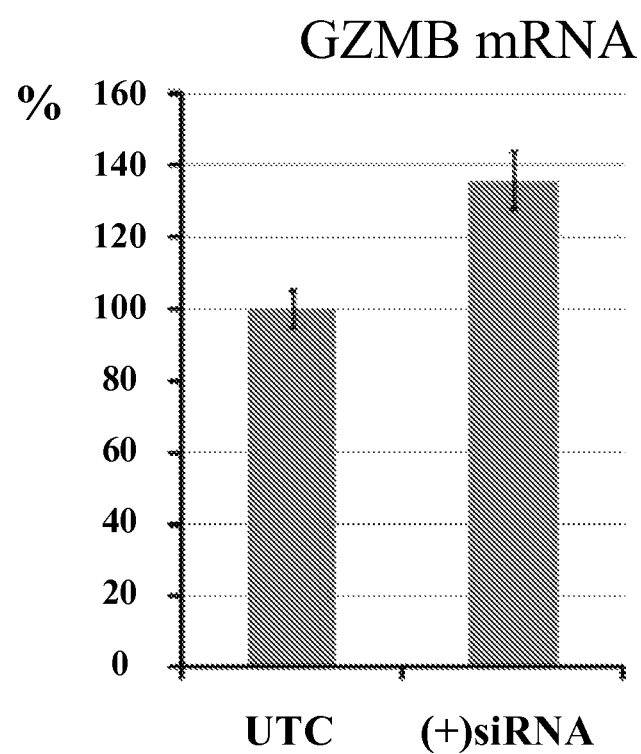
FIG. 27 shows RT-PCR results for GZMB mRNA following treatment of HeLa cells with Fen1 siRNA.

As illustrated in FIG. 27, the level of GZMB mRNA was moderately increased at approximately 30% in siRNA-transfected cells as compared to untreated control (UTC). This result is consistent with the data shown that most miRNAs suppress gene expression (Chekulaeva et al., *Curr. Opin. Cell Biol.*, 2009, 21, 452-460).

Example 18

Depiction of miRNAs Potentially Targeting GZMM 3' UTR Region

Figure 28:
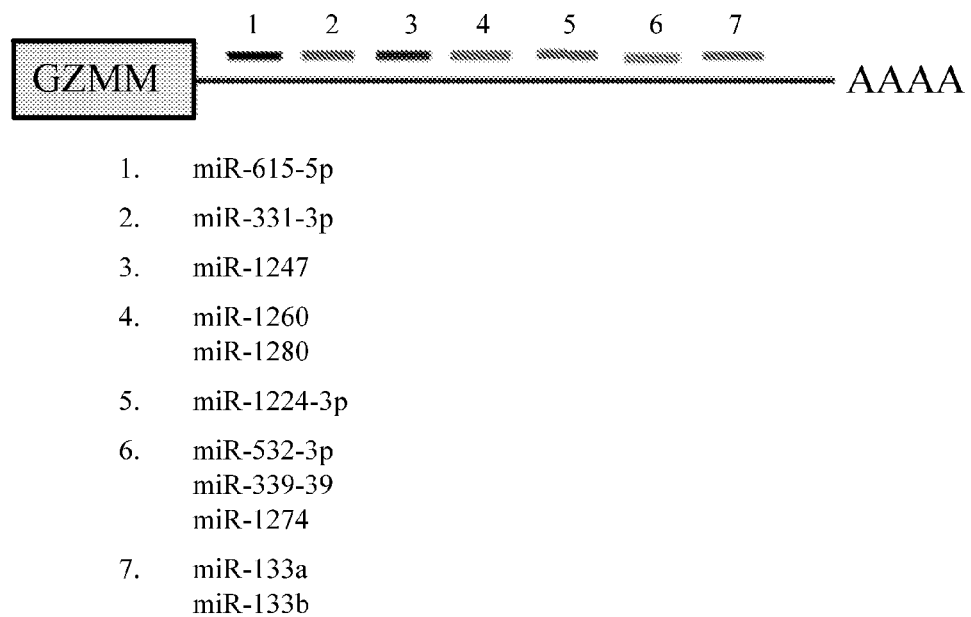
FIG. 28 shows a schematic depiction of the relative positions that miRNAs may potentially target the GZMM 3' UTR.

Schematic depiction of miRNAs potentially targeting GZMM 3' UTR region is illustrated in FIG. 28. The relative positions of miRNAs are indicated with colored bars, and names are shown with the corresponding colors. The gray box indicates the coding region of the mRNA.

As depicted, the 3' UTR of GZMM can be potentially targeted by eleven miRNAs, as predicted using a web-based server TargetScan (http://www.targetscan.org/). Six miRNAs (miR-133, miR-331, miR-339, miR-532, mir- and 615) were selected, tested and evaluated as illustrated in the following example (Example 19).

Example 19

Effect of siRNA Transfection on miRNA Levels in HeLa Cells

HeLa cells were transfected for 48 hours at 8 nM concentration with Fen1 siRNA (HSS176903) from Example 4 using the transfection methods as described in Example 1. Levels of six tested miRNAs (miR-133, miR-331, miR-339, miR-532, mir- and 615) were detected using qRT-PCR as described in Example 1. The results are presented in FIG. 29.

Figure 29:
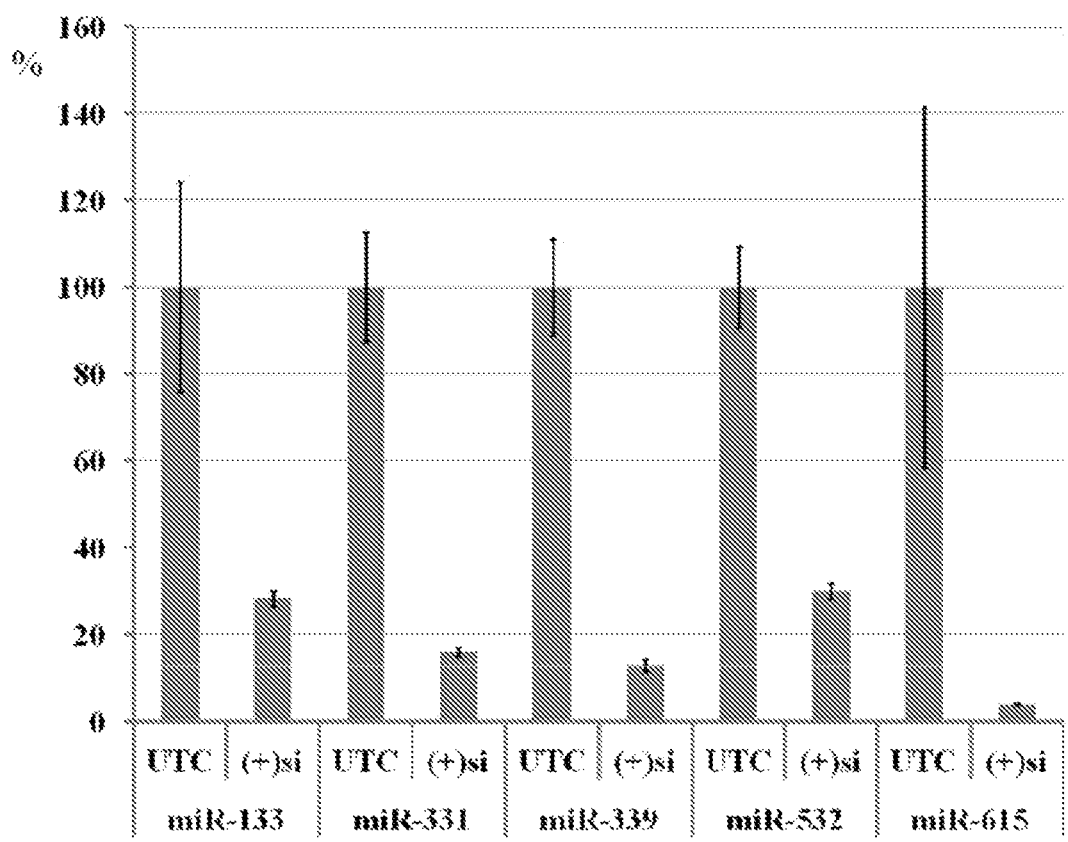
FIG. 29 shows miRNA levels following treatment of HeLa cells with Fen1 siRNA relative to miRNA levels in untreated control HeLa cells.

As illustrated in FIG. 29, the levels of the six tested miRNAs were significantly reduced upon siRNA transfection as compared to untreated control (UTC). This result suggests that the effect of siRNAs on miRNAs is broad.

Example 20

Role of GZMM Protease in siRNA-Induced Tubulin Reduction

To examine the effect of siRNAs on GZMM and α-tubulin levels, HeLa cells were transfected at 8 nM concentration for 24 hours with PTEN or Fen1 siRNA (ISIS 341401 or HSS176903). Levels of GZMM mRNA were determined by qRT-PCR. GZMM and α-tubulin protein levels were analyzed by western blot. hnRNP A2 was used as a loading control. The methods used to perform this assay are described in Example 1. The results are presented in FIGS. 30 and 31. "UTC" indicates untreated control. "Fen-1 siRNA" indicates cells transfected with siRNA HSS176903 targeting Fen1. "PTEN-siRNA" indicates cells transfected with ISIS 341401 targeting PTEN.

Figure 30:
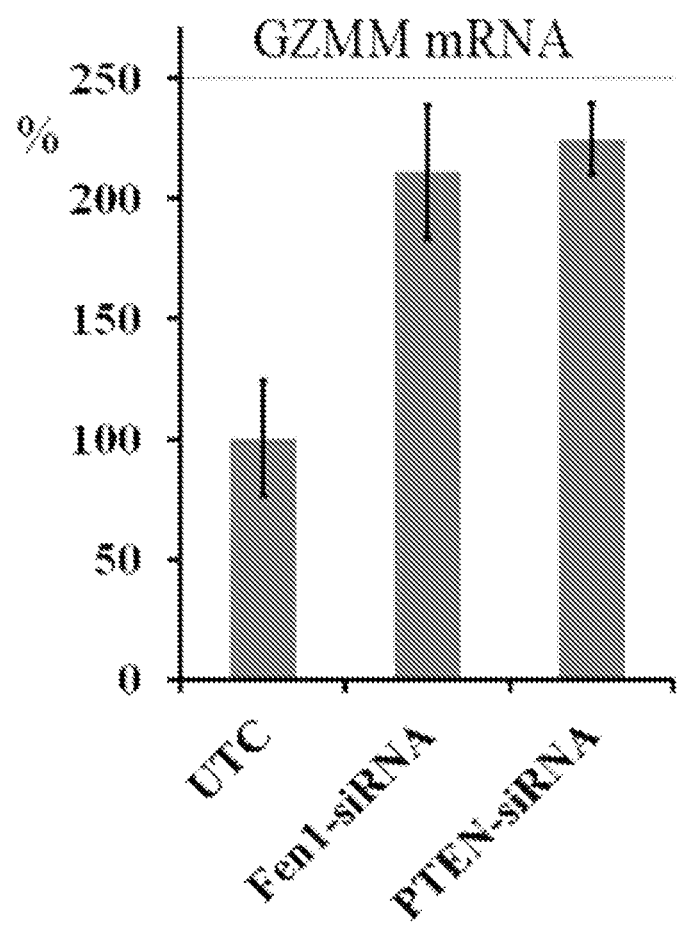
FIG. 30 shows RT-PCR results for GZMM mRNA following treatment of HeLa cells with siRNA.
Figure 31:
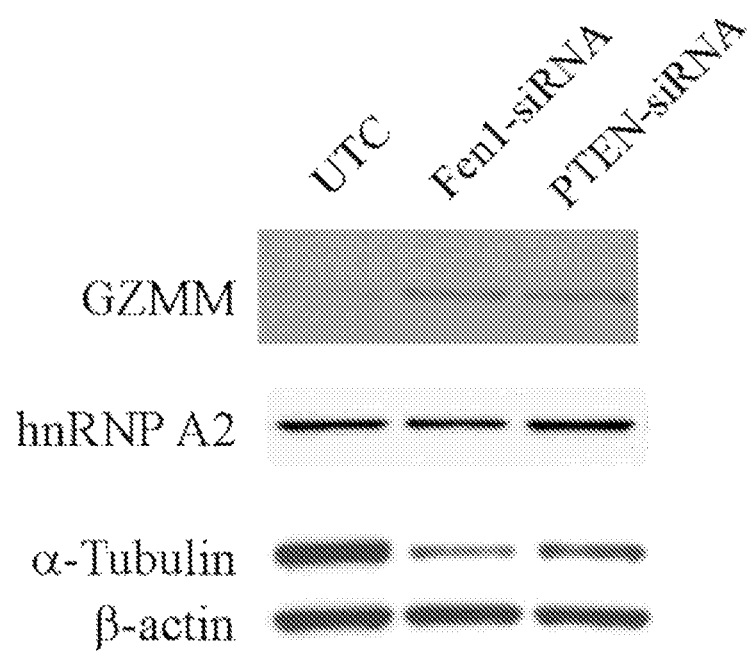
FIG. 31 shows a western blot illustrating protein levels following treatment of HeLa cells with siRNA.

As illustrated in FIGS. 30 and 31, increased levels of GZMM mRNA and protein and decreased levels of α-tubulin were observed in siRNA-transfected cells as compared to untreated control (UTC).

Taken together, results from Examples 15-20 suggest that siRNA-induced degradation of α-tubulin may result from up-regulation of GZMB and/or GZMM.

Example 21

Role of GZMB and GZMM on siRNA-Induced Tubulin Reduction

To examine the role of GZMB and GZMM on siRNA-induced tubulin reduction, several siRNAs were selected and evaluated.

siRNAs

The synthesis and purification of U16 siRNA was performed using similar methods as described in Baker et al., *J. Biol. Chem*, 272, 11994-12000. Unless otherwise stated, the pre-designed siRNAs were purchased from commercial sources and the composition of the sense trand is presented in Table 5. Each nucleoside throughout the oligonucleotide is ribonucleosides and all the internucleoside linkages are phosphodiester (P=O) linkages.

Cell Culture, Transfection and Analysis

HeLa cells were transfected with 0.75 nM concentration of siRNAs from Table 5 targeting U16, GZMB, or GZMM alone; or 0.5 nM concentration each of GZMB and GZMM siRNAs (HSS104647 or HSS179158) for co-depletion. After 36 hours, 8 nM concentration of Fen1 siRNA (HSS176903) was transfected. Cells were harvested 16 hours post transfection and protein levels were detected by western analysis as described in Example 1. The effect of reducing these proteases on Fen1 siRNA induced α-tubulin reduction was analyzed, and tubulin level was detected by western analysis, shown in FIG. 32. The signal strength was measured using ImageJ and plotted either as raw data (blue bars) or normalized to γ-tubulin (red bars) in FIG. 33. The error bars represent standard deviation of three parallel experiments.

Figure 32:
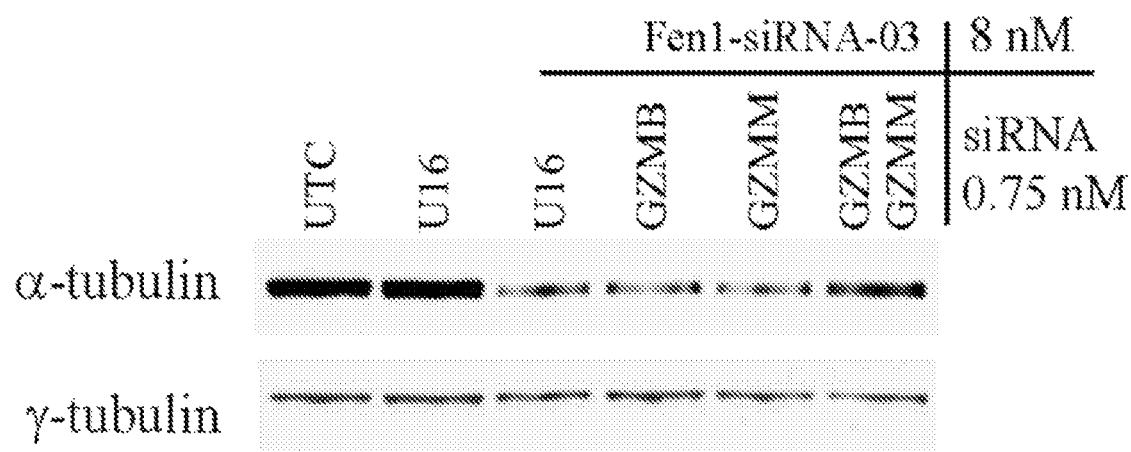
FIG. 32 shows a western blot illustrating tubulin protein levels following individual and combination treatment of HeLa cells with GZMB, GZMM, and Fen1 siRNA.
Figure 33:
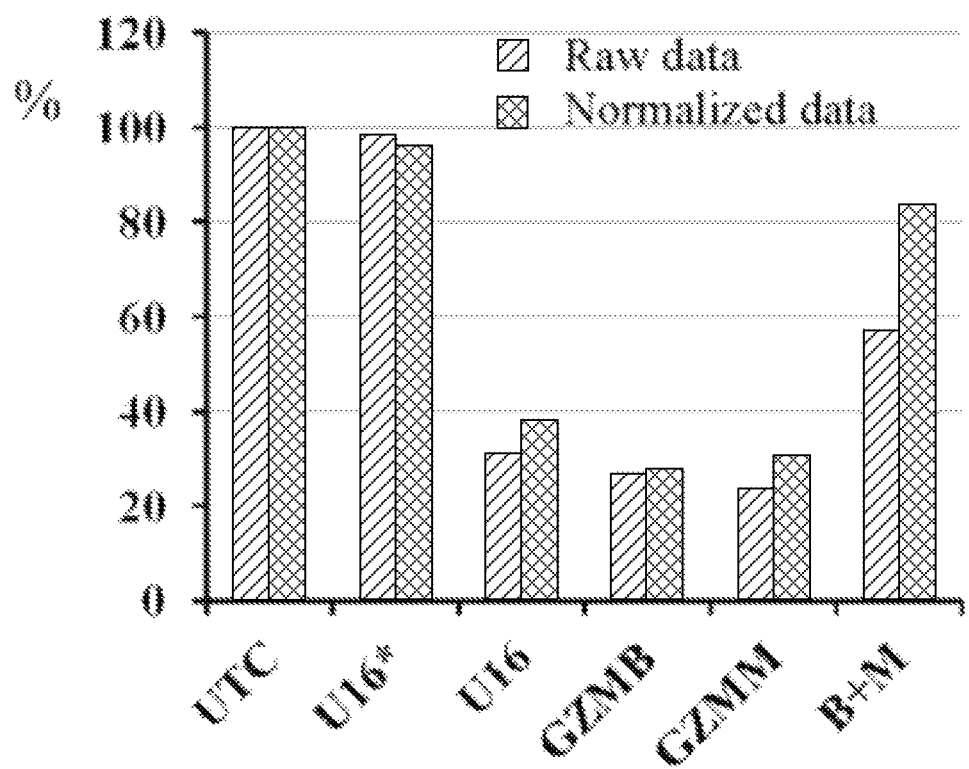
FIG. 33 shows quantification of α-tubulin protein levels normalized to γ-tubulin protein levels in the western blot depicted in FIG. 32.

As illustrated in FIGS. 32 and 33, simultaneous reduction of GZMB and GZMM partially suppressed siRNA-induced tubulin reduction. Although granzyme mRNAs were significantly reduced by more than 80% in cells treated with the corresponding siRNAs (data not shown), reduction of either GZMB or GZMM had no significant effect on tubulin reduction, similar to the control siRNA (U16) treated cells. However, co-depletion of the two proteases partially restored α-tubulin level to approximately 60% of normal, suggesting that GZMB and GZMM may have redundant roles in α-tubulin degradation, and that siRNA-induced tubulin reduction is at least partially due to up-regulation of the two proteases.

TABLE 5 siRNAs used to evaluate the role of GZMB and GZMM on siRNA-induced tubulin reduction

| siRNA cat. no. | Target | Company | Composition (only sense strand is shown) | SEQ ID NO. |
| --- | --- | --- | --- | --- |
| HSS176903 | Fen1-03 | Invitrogen | 5'-CAGGAACAGUUUGUGGAUCUGUGCA | 59 |
| U16 | U16 | ISIS Pharm. | 5'-GGCAACUGUCGCUGAGAACA-3' | 63 |
| HSS104647 | GZMB | Invitrogen | 5'-CCUACAUGGCUUAUCUUAUGAUCUG-3' | 64 |
| HSS179158 | GZMM | Invitrogen | 5'-CAGCCAUCCAGCACCCUCGCUACAA-3' | 65 |

The invention claimed is:

1. A method for identifying a competitive microRNA modulating compound comprising:
performing an assay to determine whether a test compound is capable of competing with at least one microRNA for a microRNA-associated protein, wherein the assay comprises measuring the amount and/or activity of at least one microRNA in a cell and at least one object protein in a cell; wherein
if the test compound modulates the amount and/or activity of at least one microRNA in the cell and modulates the amount or activity of protease granzyme B in the cell, then it is a competitive microRNA modulating compound.

2. The method of claim 1, wherein the microRNA-associated protein is Ago2.

3. The method of claim 1, wherein the microRNA-associated protein is nucleolin.

4. The method of claim 1, wherein the microRNA-associated protein is nucleophosmin.

5. The method of claim 1, wherein the microRNA-associated protein is Rat1p.

6. The method of claim 1, wherein the microRNA-associated protein is XRN2.

7. The method of claim 1, wherein the competitive microRNA modulating compound decreases the amount and/or activity of at least one microRNA in the cell.

8. The method of claim 1, wherein the competitive microRNA modulating compound increases the amount and/or activity of at least one microRNA in the cell.

9. The method of claim 1, wherein the microRNA modulating compound reduces the amount of α-tubulin in the cell.

10. The method of claim 1, wherein the test compound is a small molecule.

11. The method of claim 1, wherein the test compound is an oligomer.

12. The method of claim 1, wherein the test compound is an oligonucleotide.

13. The method of claim 12, wherein the oligonucleotide is double-stranded.

14. The method of claim 12, wherein the oligonucleotide is single-stranded.

15. The method of claim 12, wherein the oligonucleotide comprises at least one RNA nucleoside.

* * * * *